(12) United States Patent
Forrow

(10) Patent No.: US 8,163,146 B2
(45) Date of Patent: Apr. 24, 2012

(54) MEDIATOR STABILIZED REAGENT COMPOSITIONS FOR USE IN BIOSENSOR ELECTRODES

(75) Inventor: Nigel J. Forrow, Abingdon (GB)

(73) Assignee: Abbott Diabetes Care Inc., Alameda, CA (US)

( * ) Notice: Subject to any disclaimer, the term of this patent is extended or adjusted under 35 U.S.C. 154(b) by 639 days.

(21) Appl. No.: 11/871,826

(22) Filed: Oct. 12, 2007

(65) Prior Publication Data

US 2009/0095625 A1 Apr. 16, 2009

(51) Int. Cl.
G01N 27/327 (2006.01)
G01N 27/416 (2006.01)

(52) U.S. Cl. .................. 204/403.01; 205/792; 204/280

(58) Field of Classification Search .......... 204/403.01–403.15, 280; 205/777.5, 205/778, 792; 435/4–40.52, 173.4–173.6, 435/183, 190, 287.1–288.7; 436/62–71, 436/500–548
See application file for complete search history.

(56) References Cited

U.S. PATENT DOCUMENTS

| 5,262,305 | A | 11/1993 | Heller et al. |
| 5,264,104 | A | 11/1993 | Gregg et al. |
| 5,320,725 | A | 6/1994 | Gregg et al. |
| 5,356,786 | A | 10/1994 | Heller et al. |
| 5,593,852 | A | 1/1997 | Heller et al. |
| 5,665,222 | A | 9/1997 | Heller et al. |
| 5,972,199 | A | 10/1999 | Heller et al. |
| 6,103,033 | A | 8/2000 | Say et al. |
| 6,120,676 | A | 9/2000 | Heller et al. |
| 6,134,461 | A | 10/2000 | Say et al. |
| 6,143,164 | A | 11/2000 | Heller et al. |
| 6,175,752 | B1 | 1/2001 | Say et al. |
| 6,338,790 | B1 | 1/2002 | Feldman et al. |
| 6,736,957 | B1 | 5/2004 | Forrow et al. |
| 6,746,582 | B2 | 6/2004 | Heller et al. |
| 2002/0061599 | A1* | 5/2002 | Elling et al. .................. 436/518 |
| 2004/0079653 | A1 | 4/2004 | Karinka et al. |
| 2006/0201805 | A1 | 9/2006 | Forrow et al. |

FOREIGN PATENT DOCUMENTS

EP 1398386 A1 3/2004
WO WO2007058999 A1 5/2007

OTHER PUBLICATIONS

Rohrscheid et al. "Potential Electron Transfer Complexes of the [M-O4] Type: Synthesis and Properties of Complexes Derived from Pyrocatechol and Tetrachloropyrocatechol" Inorg. Chem., 1966, 5 (9), pp. 1542-1551.*

Hendenmo et al. "Reagentless Amperometric Glucose Dehydrogenase Biosensor Based on Electrocatalytic Oxidation by NADH by Osmium Phenanthrolinedione Mediator" Analyst, 1996, vol. 121, pp. 1891-1895.*

(Continued)

*Primary Examiner* — Kaj K Olsen
*Assistant Examiner* — Susan D Leong
(74) *Attorney, Agent, or Firm* — Edward J. Baba; Khin K. Chin; Bozicevic, Field & Francis LLP

(57) ABSTRACT

The claimed subject matter relates to the stabilization of 1,2-quinone mediators, especially those containing 1,10-phenanthroline quinone (PQ) and more especially transition metal complexes of PQ, in the presence of enzymes when contained in dry reagent layers for biosensor electrodes, through the use of various metal salts, particularly those of lithium.

17 Claims, 16 Drawing Sheets

Two example modes of co-ordination of metal ions, $M^{n+}$, to the carbonyl oxygen atoms of a nickel complex of PQ for the purpose of inhibiting reaction with amines.

OTHER PUBLICATIONS

Breikss, A., et al. Electrochemical and mechanistic studies of tricarbonylchloro(4,4'-dimethyl-2,2'-bipyridine)rhenium and their relation to the catalytic reduction of carbon dioxide. Journal of Electroanalytical Chemistry and Interfacial Electrochemistry. 1986, vol. 201, No. 2, pp. 347-358.

Eckert, T., et al. Chemical properties of phenanthrolinequinones and the mechanism of amine oxidation by o-quinones of medium redox potentials. Journal of the American Chemical Society. 1983, vol. 105, pp. 4431-4441.

Evans, D., et al. Effect of metal ions on the electrochemical reduction of some heterocyclic quinones. Journal of Electroanalytical Chemistry and Interfacial Electrochemistry. 1982, vol. 136, No. 1, pp. 149-157.

Forrow, N., et al. Development of a commercial amperometric biosensor electrode for the ketone D-3-hydroxybutyrate. Biosensors and Bioelectronics. 2005, vol. 20, pp. 1617-1625.

Goss, C., et al. Spectral, electrochemical and electrocatalytic properties of 1,10phenanthroline-5,6-dione complexes of transition metals. Inorganic Chemistry. 1985, vol. 24, No. 25, pp. 4263-4267.

Itoh, S., et al. Effects of metal ions on the electronic, redox, and catalytic properties of cofactor TTQ of quinoprotein amine dehydrogenases. J Am Chem Soc. 2000, vol. 122, pp. 12087-12097.

Itoh, S., et al. Catalytic effect of monovalent cations on the amine oxidation by cofactor TTQ of quinoprotein amine dehydrogensases. Chem Commun. 2000, issue 5, pp. 329-330.

Lei, Y., et al. Effects of coordination to transition metals on the hydration and electroactivity of the chelating ligand 1,10-phenanthroline-5,6-dione. Inorganic Chemistry. 1996, vol. 35, No. 10, pp. 3044-3049.

Lorenzo, E., et al. Analytical strategies for amperometric biosensors based on chemically modified electrodes. Biosensors and Bioelectronics. 1998, vol. 13 (3-4), pp. 319-332.

Oku, K., et al. Interaction between trehalose and alkaline-earth metal ions. Biosci Biotechnol Biochem. 2005, vol. 69, No. 1, pp. 7-12.

Pan, Q., et al. Synthesis and properties of Mn(II), Fe(II), Co(II) complexes with dichloride and 1, 10-phenanthroline-5,6-dione. Huaxue Yanjiu. 2003, vol. 14, No. 2, pp. 32-34.

Paw, et al. Synthesis, characterization, and spectroscopy of dipyridocatecholate complexes of platinum. Inorganic Chemistry. 1997, vol. 36, No. 11, pp. 2287-2293.

Paw, et al. Dipyridocatecholate-bridged complexes of platinum and ruthenium diiimine chromophores. Inorganic Chemistry. 1998, vol. 37, No. 16, pp. 3919-3926.

Shi, M., et al. Adsorption/deposition of the ligands 1,10-phenanthroline-5,6-dione and 1,10-phenanthroline-5,6-diol and their metal complexes on pyrolytic graphite electrodes. Analytical Chemistry. 1998, vol. 70, No. 8, pp. 1489-1495.

Wrighton, M., et al. Nature of the lowest excited state in tricarbonylchloro-1, 10-phenanthrolinerhenium(I) and related complexes. Journal of the American Chemical Society. 1974, vol. 96, No. 4, pp. 998-1033.

Wu, Q., et al. Electroanalytic oxidation of NADH at glassy carbon electrodes modified with transition metal complexes containing 1,10-phenanthroline-5,6-dione ligands. Analytical Chemistry. 1996, vol. 68, No. 20, pp. 3688-3696.

* cited by examiner

Two example modes of co-ordination of metal ions, $M^{n+}$, to the carbonyl oxygen atoms of a nickel complex of PQ for the purpose of inhibiting reaction with amines.

MEDIATOR STABILIZED REAGENT COMPOSITIONS FOR USE IN BIOSENSOR ELECTRODES

TECHNICAL FIELD

The claimed subject matter relates to the stabilization of redox mediators incorporated into reagent layers used in enzyme-based biosensor electrodes.

BACKGROUND

A basic enzyme-based biosensor electrode typically comprises a base conducting electrode system (carbon, gold, platinum, etc.) on an insulating substrate surmounted by a reagent layer containing at least a redox enzyme/cofactor (GDH/NAD, HBDH/NAD, GOx/FAD, GDH/PQQ, GDH/FAD) which acts on an analyte (glucose, 3-hydroxybutyrate, etc.) and a redox mediator which provides electrical communication between the enzyme/cofactor and the electrode. The action of enzyme/cofactor on the analyte results in the conversion of oxidized mediator to its reduced form which, in turn, is oxidized at an electrode. This generates an electrical signal which is proportional to the analyte concentration.

Commercial biosensor electrodes are manufactured on a large-scale using multi-stage processes of which reagent layer deposition is just one step. The reagent composition is required to be stable during manufacturing. Furthermore, the final packaged biosensor electrodes containing the dry reagent layer will be subjected to quality testing, shipping, distribution and storage such that it may be several months before the customer uses the product. Ideally, the shelf life of the biosensor electrode is in excess of 18 months from the date of manufacture. The stability of the biosensor electrode must be maintained during this period.

A common issue encountered by biosensor manufacturers is that the redox mediator, if in the oxidized form, tends to convert to the reduced form in the dry reagent layer over time (see, e.g., WO 2007/058999, EP 1398386). The problem is exacerbated in biamperometric systems where high concentrations of oxidized mediator are required for reduction by both the enzyme/cofactor and the reference electrode during the assay.

Furthermore, modern biosensor electrodes have fast assay times (5 seconds or less). This creates additional sensitivity of the reduced mediator in the reagent layer since it is immediately oxidized upon application of the electrode operating potential at the start of the assay. The result is an elevated background response, which varies over time such that the determination of low analyte concentrations in test samples can be inaccurate. Accordingly, there is a need in the art for methods and compositions that act to stabilize redox mediators in the presence of enzymes, when contained in dry reagent layers of biosensor electrodes. Such mediators may include, but are not limited to 1,2-quinone mediators, especially those containing 1,10-phenanthroline quinone (PQ), and more especially transition metal complexes of PQ.

1,2-Quinone compounds are known to be reactive toward nucleophiles via a variety of mechanisms. For example, U.S. Pat. No. 6,736,957 reports that many 1,2-quinones can react irreversibly with protein thiol groups leading to enzyme inactivation. This is avoided by PQ-type 1,2-quinones resulting in improved biosensor electrode stability (see, e.g., Forrow et al. (2005) *Biosensors & Bioelectronics* 20:1617-1625 for further discussion).

PQ-type mediators and other 1,2-quinones are also known to be susceptible to reduction by amines (see, e.g., Itoh et al. (1983) *J. Am. Chem. Soc.* 105:4431-4441). PQ-type mediator reaction with and consequent reduction by amines present in the biosensor reagent layer represents a major route toward conversion to the reduced mediator form.

This is due to the fact that amine functional groups are present in enzymes (e.g., lysine side-chains, terminal amino group), some stabilizers (e.g., proteins such as BSA, hydrolysed gelatin) and many buffer salts (e.g., TRIS, BES). Mediator reaction with enzyme amine groups may also lead to enzyme denaturation, cross-linking or inactivation (if the groups are involved in substrate or cofactor binding), i.e., another mode of biosensor electrode destabilization. FIG. 3 illustrates the mechanism of reaction of a PQ-type quinone with a primary amine (e.g., lysine side-chain) leading to the formation of a reduced aminoalcohol species, also pictured in the scheme below:

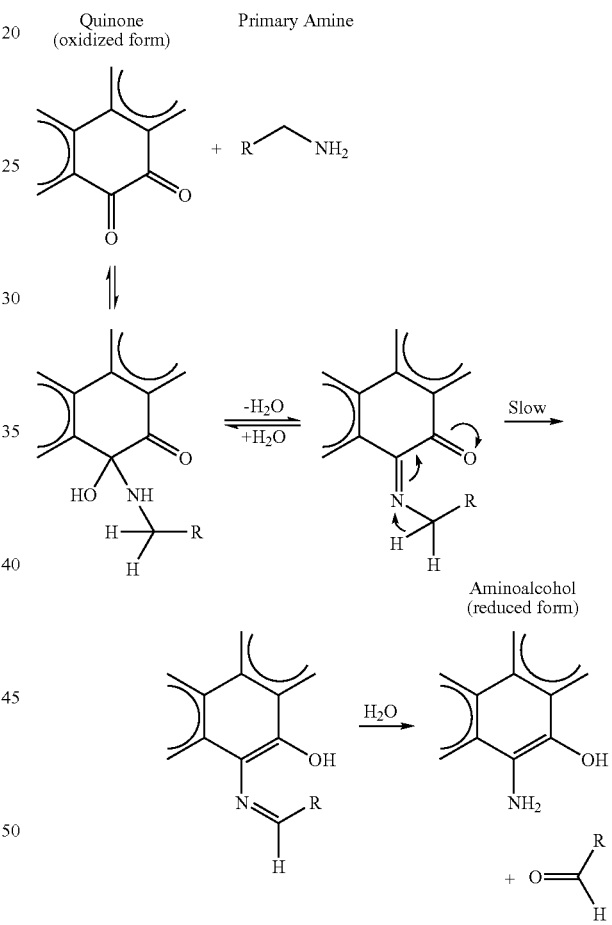

SUMMARY

The claimed subject matter is based on the discovery that salts of certain metal ions act as stabilizers for 1,2-quinone-type mediators, particularly those containing 1,10-phenanthroline quinone (PQ), and more especially transition metal complexes of PQ such as $[Ni(PQ)_3]^{2+}$.

Such metal ions include, but are not limited to $Li^+$, $Be^{2+}$, $Mg^{2+}$, $Ca^{2+}$, $Sr^{2+}$, $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$ and $Lu^{3+}$.

The metal ions of embodiments of the invention can be used as stabilizers in a number of commercially important applications, such as, inter alia, the development and manufacture of biosensors, and stable reagent chemistry for biosensor gold strips. Such metal ions may be used to stabilize redox mediators contained in the dry reagent layers of biosensor electrodes when amine-containing compounds, such as enzymes, are present.

Without being confined to a definite mechanism or theory, it is postulated that the salts of these metal ions minimize the amount of reduced mediator formed during storage of biosensor electrodes. It is speculated that these metal ions coordinate weakly with the 1,2-quinone carbonyl groups, thereby inhibiting their reaction with and consequent reduction by any amine groups present in the biosensor reagent layer. Conversely, it is also envisioned that these metal ions could interact themselves with amine groups, thereby inhibiting their reaction with and consequent reduction of 1,2-quinone carbonyl groups. Furthermore, a combination of these two mechanisms could be present.

Accordingly, in one embodiment the invention provides metal ions and their salts which are capable of stabilizing high concentrations of 1,2-quinone-type mediators, particularly PQ and more especially transition metal complexes of PQ, in the presence of amine-containing components, such as enzymes contained in dry reagent layers of biosensor electrodes. The biosensor electrode products of embodiments of the invention, which use PQ-type redox mediators containing a stabilizing metal ion, preferably lithium, have stable responses at low glucose. As will be described in further detail below, in the absence of one of the metal ions mentioned above, the low glucose response of a biosensor electrode product containing a PQ-type mediator is not stable.

An aspect of an embodiment of the invention relates to methods for stabilizing a redox mediator, comprising adding a metal salt to a redox mediator either in situ or in solution, wherein the metal salt and redox mediator are combined during the manufacture of biosensors, i.e., biostrips, including biamperometric and amperometric strips. The salt comprises a stabilizing metal ion weakly associated with the redox mediator and/or enzyme, and the redox mediator comprises a 1,2-quinone. If the 1,2-quinone is 1,10-phenanthroline quinone (PQ), the redox mediator may be covalently associated with a coordinating metal ion, such as those illustrated later in the disclosure.

By way of example, the metal ions are incorporated with a PQ-type mediator (most preferably the nickel complex of PQ) and an enzyme/cofactor into a reagent coating solution used to deposit a stable reagent film on a gold electrode (such as, for example, via a slot-coating technique). The resulting biostrip will have acceptable stability for a commercial biosensor electrode product with a shelf life of at least 18 months. Example A sets forth reagent formulations containing the metal ion stabilizers of an embodiment of the claimed subject matter. The preferred enzymes/cofactors are those which utilise $NAD(P)^+$ as a cofactor, such as, for example, NAD-GDH and NAD-HBDH, though others such as FAD-GDH may also be used.

These and other objects, advantages, and features of the claimed subject matter will become apparent to those persons skilled in the art upon reading the details of the subject matter claimed, as more fully described below.

BRIEF DESCRIPTION OF THE DRAWINGS

Aspects and embodiments of the invention are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

Figure 1:
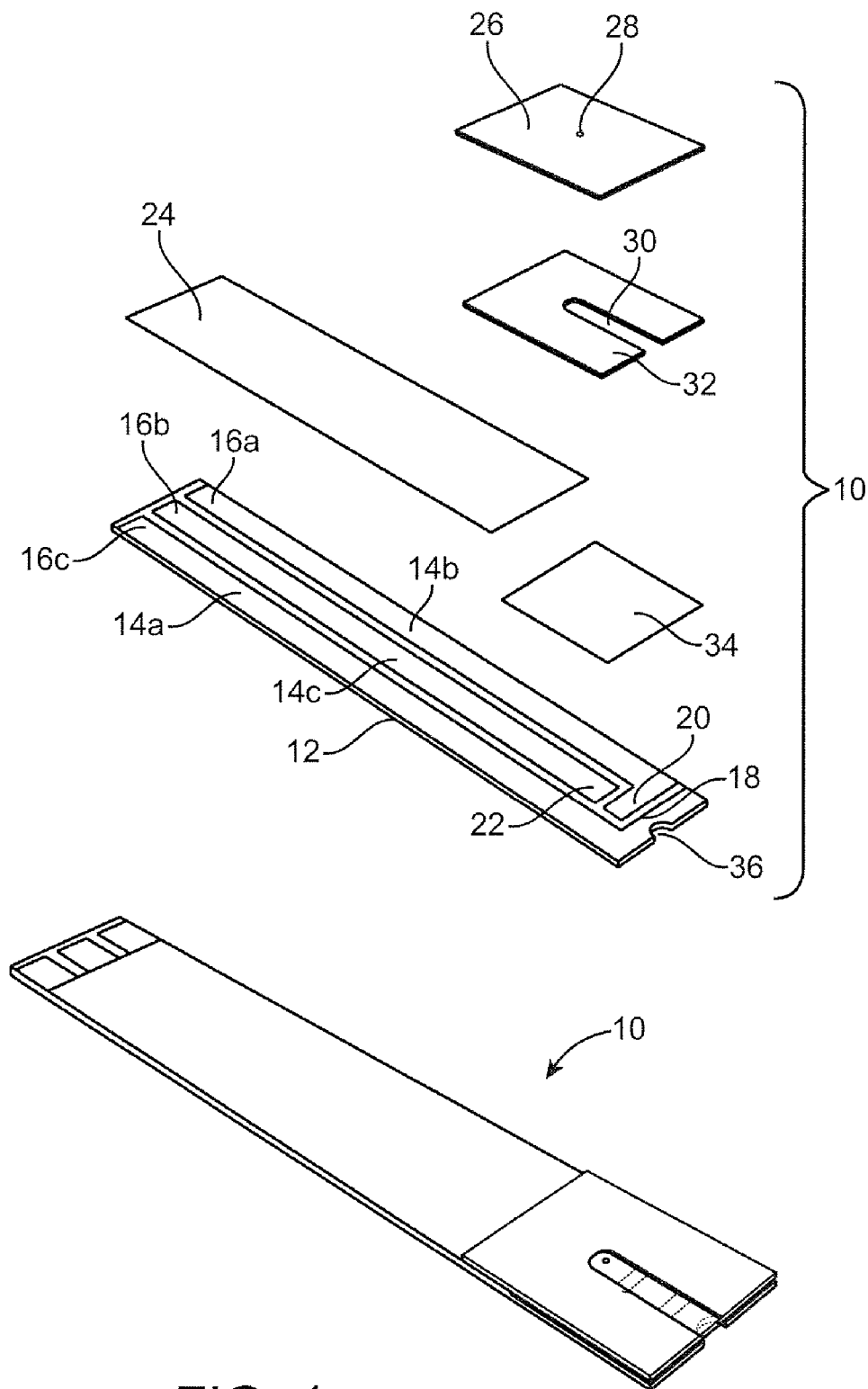
FIG. 1 is a schematic diagram that illustrates a perspective view of a biamperometric strip containing a combined working/reference layer.

Before the reagents and formulations of the claimed subject matter are described, it is to be understood that this invention is not limited to any particular embodiment described, and as such may, of course, vary. It is also to be understood that the terminology used herein is with the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the claimed subject matter. The upper and lower limits of these smaller ranges may independently be included or excluded in the range, and each range where either, neither or both limits are included in the smaller ranges is also encompassed within the claimed subject matter, subject to any specifically excluded limit in the stated range. Where the stated range includes one or both of the limits, ranges excluding either or both of those included limits are also included in embodiments of the invention.

Unless defined otherwise, all technical and scientific terms used herein have the same meaning as commonly understood by one of ordinary skill in the art to which claimed subject matter belongs. Although any methods and materials similar or equivalent to those described herein can be used in the practice or testing of the claimed subject matter, the preferred methods and materials are now described. All publications mentioned herein are incorporated herein by reference to disclose and describe the methods and/or materials in connection with which the publications are cited. The present disclosure is controlling to the extent there is a contradiction between the present disclosure and a publication incorporated by reference.

It must be noted that as used herein and in the appended claims, the singular forms "a", "and", and "the" include plural referents unless the context clearly dictates otherwise. Thus, for example, reference to "a peptide" includes a plurality of such peptides and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the claimed subject matter is not entitled to antedate such publication by virtue of prior claimed subject matter. Further, the dates of publication provided may be different from the actual publication dates which may need to be independently confirmed.

DEFINITIONS

As used herein, the expression "transition metal" means those elements of a metallic nature that have partially filled d shells in any of their commonly occurring oxidation states and includes elements with atomic numbers in the ranges 21-30, 39-48 and 72-80. The expression "lanthanides" or "lanthanoid" means those elements of a metallic nature with atomic numbers in the range 57-71. The expression "rare earth metal" comprises a collection of sixteen naturally occurring elements including the transition metals scandium (atomic number 21) and yttrium (atomic number 39) together with fourteen of the fifteen lanthanides or lanthanoids, excluding the radioactive promethium with no stable isotopes. The expression "heavier alkaline earth metals" means those elements of a metallic nature that are in the IIA column of the periodic table and that have an atomic number equal to or higher than 20.

By "protein" is meant a sequence of amino acids for which the chain length is sufficient to produce the higher levels of tertiary and/or quaternary structure. This is to distinguish from "peptides" or other small molecular weight drugs that do not have such structure. Typically, a protein will have a molecular weight of about 15-200 kD. An enzyme is a type of protein which catalyses the conversion of a substrate molecule such as glucose for example into a product molecule such as gluconolactone for example.

The terms "treatment", "treating" and the like are used herein to refer to both therapeutic treatment and prophylactic or preventative measures. Those in need of treatment include those already with the disorder as well as those in which the disorder is to be prevented. In general, this encompasses obtaining a desired pharmacologic and/or physiologic effect, e.g., stimulation of angiogenesis. The effect may be prophylactic in terms of completely or partially preventing a disease or symptom thereof and/or may be therapeutic in terms of a partial or complete cure for a disease and/or adverse effect attributable to the disease. The terms as used herein cover any treatment of a disease in a mammal, particularly a human, and include: (a) preventing a disease or condition (e.g., preventing the loss of cartilage) from occurring in a subject who may be predisposed to the disease but has not yet been diagnosed as having it; (b) inhibiting the disease, e.g., arresting loss of cartilage; or (c) relieving the disease (e.g., enhancing the development of cartilage).

The terms "subject," "individual," "patient," and "host" are used interchangeably herein and refer to any vertebrate, particularly any mammal and most particularly including human subjects, farm animals, and mammalian pets. The subject may be, but is not necessarily under the care of a health care professional such as a doctor.

A "stable" formulation is one in which the protein or enzyme therein essentially retains its physical and chemical stability and integrity upon storage and exposure to relatively high temperatures. Various analytical techniques for measuring peptide stability are available in the art and are reviewed in *Peptide and Protein Drug Delivery*, 247-301, Vincent Lee Ed., Marcel Dekker, Inc., New York, N.Y., Pubs. (1991), and Jones, A. (1993) *Adv. Drug Delivery Rev.* 10:29-90. Stability can be measured at a selected temperature for a selected time period.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the claimed methods and compositions. This includes chronic and acute disorders or diseases including those pathological conditions which predispose the mammal to the disorder in question. Non-limiting examples of disorders to be treated herein include type I and type II diabetes mellitus.

DETAILED DESCRIPTION OF THE PREFERRED EMBODIMENTS

The claimed subject matter is based on the discovery that salts of certain metal ions act as stabilizers for 1,2-quinonetype mediators, particularly those containing PQ, and more especially transition metal complexes of PQ such as [Ni(PQ)$_3$]$^{2+}$. This is accomplished through the use of various metal salts, particularly those of lithium.

In one embodiment, the stabilizing metal ion is mixed with the quinone in solution, i.e., in situ. Alternatively, in another embodiment, the quinone and stabilizing metal salt are mixed together in the solid state by some such means as stirring/grinding/ball-milling to form an intimate mixture and then added together to the solution.

The use of lithium and lanthanide metal ions as stabilizers in the PQ system is novel. There is no report to date of the use of non-transition metal ions to stabilize transition metal complexes of PQ, and in particular, the nickel complex.

U.S. Published Patent Application No. 20040079653 ("the '653 application") describes the use of Mn$^{2+}$, Fe$^{2+/3+}$, Co$^{2+}$, Os$^{2+/3+}$, Ru$^{2+/3+}$, Ca$^{2+}$, Sr$^{2+}$, Ba$^{2+}$ for improvement of oxygen and haematocrit biases in PQ-containing strips. U.S. Published Patent Application No. 20060201805 is a continuation of the '653 application, in which Ni$^{2+}$ is additionally claimed.

These applications concern the use of the specified metal ions for the intended purpose of coordination to the nitrogen atoms, but not the oxygen atoms of PQ. The coordinating metal ion may be added to a formulation containing PQ. Alternatively, the pre-formed and isolated metal-PQ complex is added to the formulation. It is important to note that only one metal ion is involved in this scheme. This improves the electrochemistry of PQ while also resulting in improved strip performance; however, these applications do not address response stability.

The addition of a metal ion to a PQ-containing formulation results in variable metal-PQ complexes, depending on the PQ-to-metal ion molar ratio and the metal ion. Metal ion coordination at the PQ nitrogen atoms occurs readily; however, further metal ion coordination at the PQ oxygen atoms will occur in the presence of excess metal ion, once all of the nitrogen atom coordination sites are occupied. In the case of isolated metal-PQ complexes, it is clear that coordination occurs only at the PQ nitrogen atoms and not at the oxygen atoms. Accordingly, this scheme involves only one metal ion, which may be termed the "coordinating" metal ion.

The key aspect of the claimed subject matter is that stabilization of PQ-type mediators in the presence of amines in the solid state and in aqueous solution may be obtained through the weak coordination of certain metal ions to the oxygen atoms of PQ. This ion may be referred to as the "stabilizing" metal ion. Thus, the claimed subject matter includes two or more different metal ions—one that coordinates the PQ complex, and one that stabilizes the PQ carbonyl oxygen atoms.

There are a number of reports in the academic literature of metal (especially transition metal) complexes of PQ where coordination of the metal ion occurs exclusively at the PQ nitrogen atoms. No mention is made, however, of stabilization of PQ-type mediators in the presence of amines. Various references cited herein describe the isolation of mixed transition metal (Ru, Pd, Pt) complexes of PQ wherein coordination of the metal ions occurs at both the nitrogen and oxygen atoms of PQ. Yet, these complexes are of no use in the presently claimed subject matter since the transition metal ion binding to the oxygen atoms of PQ exerts an effect that is too strong.

Thus, in general, embodiments of the claimed subject matter provide reagent compositions that include a mediator, such as an isomer of phenanthroline quinone, 1,10-phenanthroline-5,6-dione or a derivative thereof, a coordinating metal ion, and a salt of a stabilizing metal ion which acts to stabilize the mediator. In addition, embodiments of the invention also provide biosensors that utilize the reagent composition, as well as methods of using the biosensors for detecting an analyte in a sample.

Further embodiments of the claimed subject matter provide an analyte test kit comprising a meter for measuring the concentration of an analyte, and a biosensor strip. The biosensor strip may further comprise an electrode support; a first electrode disposed on the electrode support, the first electrode being a working electrode; a second electrode disposed on the electrode support, the second electrode being a reference electrode; and a reagent composition deposited over the first electrode and second electrode.

In an aspect of an embodiment of the claimed subject matter, the reagent composition comprises an enzyme, and a redox mediator complexed with a stabilizing metal ion and a coordinating metal ion.

An aspect of an embodiment of the claimed subject matter provides a composition for use in stabilizing a biosensor comprising an enzyme and a co-factor, a salt, and a redox mediator wherein the salt and redox mediator are combined during the manufacture of the biosensor.

The salt may comprise a positively charged metal ion and a negatively charged counter ion, whereby positively charged metal ion stabilizes the redox mediator.

The salt may comprise an alkali metal or an alkaline earth metal.

The positively charged metal ion may be selected from the group consisting of lithium, scandium, yttrium, lanthanum, cerium, praseodymium, neodymium, promethium, samarium, europium, gadolinium, terbium, dysprosium, holmium, erbium, thulium, ytterbium and lutetium, but not sodium, potassium, rubidium, cesium, all other transition metals or a quaternary ammonium counter ion.

The negatively charged counter ion may be selected from the group consisting of chloride, bromide, sulfate and nitrate.

The salt may comprise a so-called "stabilizing" ion whereby the stabilizing ion is weakly associated with the redox mediator, and the redox mediator may comprise a so-called "coordinating" metal ion whereby the coordinating metal ion is covalently associated with the redox mediator.

In an aspect of an embodiment of the claimed subject matter, the stabilizing ion may be selected from the group consisting of lithium, scandium, yttrium, lanthanum, cerium, praseodymium, neodymium, promethium, samarium, europium, gadolinium, terbium, dysprosium, holmium, erbium, thulium, ytterbium and lutetium, but not sodium, potassium, rubidium, cesium, all other transition metals or a quaternary ammonium counter ion.

In an aspect of an embodiment of the claimed subject matter, the coordinating ion may be selected from the group consisting of nickel, manganese, iron, cobalt, osmium, or ruthenium.

In an aspect of an embodiment of the claimed subject matter, the ratio of salt to redox mediator is at least 1:1. In an aspect of an embodiment of the claimed subject matter, the ratio of salt to redox mediator is at least 3.7:1. In an aspect of an embodiment of the claimed subject matter, the ratio of salt to redox mediator is at least 8:1. In an aspect of an embodiment of the claimed subject matter, the ratio of salt to redox mediator is at least 10:1.

In an aspect of an embodiment of the claimed subject matter, the redox mediator is a 1,2 quinone, including 1,10-phenanthroline quinone, or a derivative thereof.

An aspect of an embodiment of the claimed subject matter provides a method for stabilizing a redox mediator, comprising adding a metal salt to a redox mediator, wherein the metal salt and redox mediator are combined during the manufacture of a biosensor. In an aspect of an embodiment of the claimed subject matter, the salt may comprise a stabilizing metal ion weakly associated with the redox mediator and a counter ion. The redox mediator may comprise a coordinating metal ion covalently associated with the redox mediator.

In an aspect of an embodiment of the claimed subject matter, the counter ion is selected from the group consisting of chloride, bromide, sulfate and nitrate.

In an aspect of an embodiment of the claimed subject matter, the enzyme is selected from the group consisting of an NAD(P)+-dependent dehydrogenase, a PQQ-glucose dehydrogenase, an FAD-glucose dehydrogenase and a glucose oxidase.

In an aspect of an embodiment of the claimed subject matter, the NAD(P)+-dependent dehydrogenase is glucose hydrogenase or hydroxybutyrate dehydrogenase.

The above disclosure sets forth a number of embodiments of the present invention. Other arrangements or embodiments, not precisely set forth, could be practiced under the teachings of the present invention.

Coordinating Metal Ions

The coordinating metal ion can be a transition metal ion or a heavier alkaline earth metal ion. Coordinating metal ions suitable for use in embodiments of the invention include, but are not limited to, nickel, manganese, zinc, calcium, iron, ruthenium, cobalt, osmium, nickel, copper, rhenium, rhodium, iridium, chromium, barium, strontium. The binding efficiencies in these complexes are dependent on the particular metal ion employed. For example, Mn (II) ions provide stronger binding than do Mg (II) ions.

A representative metal complex of 1,10-phenanthroline-5,6-dione is:

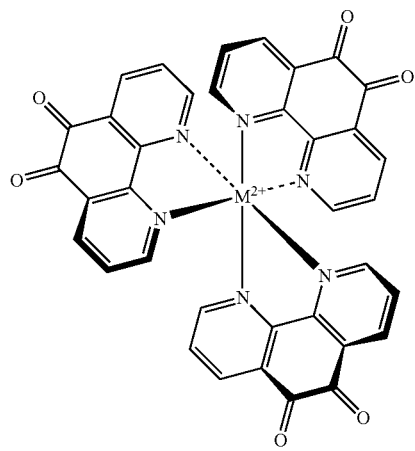

wherein M is selected from the group consisting of nickel, manganese, iron, cobalt, osmium, ruthenium, calcium, strontium, and barium.

In certain embodiments, the metal is nickel and the nickel complex of 1,10-phenanthroline-5,6-dione is:

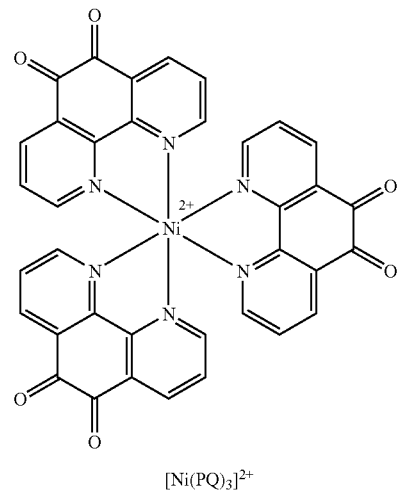

$[Ni(PQ)_3]^{2+}$

The generic formula of the complex cation is shown below. The ligands a, b, c, and d can represent two 1,10-phenanthroline-5,6-dione molecules or other monodentate ligands, such as, for example, chloride, water, ammonia, or the like, or multidentate ligands, such as, for example, bipyridyl or the like, and M, the coordinating metal ion, is selected from the group consisting of nickel, manganese, iron, cobalt, osmium, ruthenium, calcium, strontium, and barium.

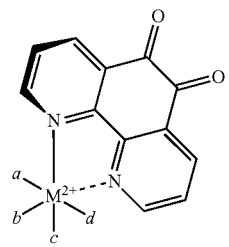

Counter anions to the coordinating metal ions suitable for use in embodiments of the invention include, but are not limited to, a halide, such as chloride, bromide, fluoride, or iodide, a nitrate, a nitrite, a sulfate, a carbonate, a phosphate, a thiocyanate, an acetate, a formate, a citrate, a succinate, an oxalate, a tartrate, a benzoate, an alkyl or aromatic sulfonate, a tungstate, a molybdate, a ferricyanide, a nitroprusside, a tetraphenylborate, an anionic dye and an anionic surfactant.

Stabilizing Metal Ions

The salts of certain metal ions have been found to act as stabilizers for 1,2-quinone-type mediators, particularly those containing PQ, and more especially transition metal complexes of PQ such as $[Ni(PQ)_3]^{2+}$.

Such metal ions include, but are not limited to $Li^+$, $Be^{2+}$, $Mg^{2+}$, $Ca^{2+}$, $Sr^{2+}$, $Sc^{3+}$, $Y^{3+}$, $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$. It is speculated that these metal ions coordinate weakly with the 1,2-quinone carbonyl groups, thereby inhibiting their reaction with and consequent reduction by any amine groups present in the biosensor reagent layer. Alternatively, it is possible that these metal coordinate weakly with any amine-containing materials in the biosensor reagent layer, thereby inhibiting their reaction with and consequent reduction of 1,2-quinone carbonyl groups.

There is a balance between achieving an adequately strong interaction between the stabilizing metal ion and the quinone carbonyl group such that reaction with amines is inhibited. Too strong of an interaction will severely affect the ability of the quinone to function as a mediator by slowing its reaction with an enzyme/cofactor and perturbing its electrochemistry. For example, it has been reported in the literature that $Mg^{2+}$ and $Ca^{2+}$ ions do not bind to the PQ carbonyl oxygen atoms in DMSO/water (1:1) while some transition metal ions ($Ni^{2+}$, $Co^{2+}$, $Zn^{2+}$) do so very strongly (Evans et al. (1982) *J. Electroanal. Chem.* 136:149-157). Consequently, most transition metal ions except $Sc^{3+}$ and $Y^{3+}$ are not ideal as stabilizers in the present context and are excluded. Another report describing the interaction of various metal ions ($Mg^{2+}$, $Ca^{2+}$, $Ba^{2+}$, $Sc^{3+}$, $Y^{3+}$) with PQ in acetonitrile solution notes that the reduction potentials of the quinone are strongly shifted in a positive direction (Yuasa et al. (2006) *Chem. Phys. Chem.* 7:942-954). U.S. Published Patent Application No. 20060201805 discloses that transition metal ions such as $Ni^{2+}$ are useful for forming complexes with the phenanthroline nitrogen atoms of PQ to derive redox mediators with beneficial properties. However, in the absence of one of the stabilizing metal ions disclosed above, PQ complexes of this type such as $[Ni(PQ)_3]^{2+}$ are still subject to adverse interactions with amine groups.

Another paper reports that lithium ions are responsible for accelerating the reaction of a 1,2-quinone with an amine in solution (Itoh et al. (2000) *Chem. Commun.* 1039:329-330). Accordingly, the particular advantage of lithium ions in stabilizing PQ-type mediators in biosensor reagent films incorporating amine-containing materials, found and presented herein, is unexpected. Furthermore, it is also of interest to note that lithium is the only Group I element which is shown herein to exert a stabilizing influence on the PQ complex. Sodium, potassium, rubidium and caesium had no effect (see, e.g., FIGS. 8 and 11).

Ammonium and quaternary ammonium salts are also excluded along with most transition metal salts since they are reactive in themselves towards carbonyl compounds such as 1,2-quinones including PQ-type mediators. For example, certain ammonium salts release ammonia which reacts with 1,2-quinones including PQ-type mediators.

The stabilizing metal ion must necessarily be coupled with a counter anion to form a salt, which is the means of adding the metal ion to the reagent formulation. In the context of the claimed subject matter, the counter anion of the stabilizing metal ion is of lesser importance and can be selected from a wide range, provided it is not reactive towards the mediator in its own right. Here, formate and acetate are excluded because of their reactivity towards PQ-type mediators. The common simple anions such as chloride, bromide, sulfate and nitrate are preferred due to the wide availability of their salts with the metal ions of the presently claimed subject matter and their low reactivity together with their high aqueous solubility.

Generally, the medium for deposition of reagents onto the biosensor electrode comprises an aqueous solution, suspension or ink which contains at least an enzyme/cofactor, redox mediator and a stabilizing salt of the claimed subject matter. The concentrations of enzyme/cofactor and redox mediator are adjusted via experimentation to provide the optimum biosensor electrode performance. In this respect, the concentration of the stabilizing metal salt is normally varied according to the required concentration of redox mediator. In theory, an ideal salt level equates to a 1:1 molar ratio of the metal ion with the 1,2-quinone redox mediator.

For transition metal complexes of PQ such as $[Ni(PQ)_3]^{2+}$, it is clear that 1 mole of redox mediator contains 3 moles of PQ leading to a theoretical requirement for 3 moles of stabilizing metal ion (salt). In one Example, 3.4% w/w $[Ni(PQ)_3]$ $Cl_2$ (mwt.=760.16) with 0.7% w/w LiCl (mwt.=42.39) is used for a reagent formulation. This equates to a 3.7:1 molar ratio of metal salt to metal-PQ complex. In practice, a slight excess of stabilizing metal salt may be required to counterbalance binding of the stabilizing metal ion by other components of the reagent formulation.

For example, it is known in the literature that metal ions do bind to trehalose (see, e.g., Oku et al. (2005) *Biosci. Biotechnol. Biochem.* 69(1):7-12) and buffer salts. Trehalose is commonly used in biosensor reagent formulations to stabilize enzymes while buffer salts control pH. Conversely, some metal ions may simultaneously interact with 2 or 3 mediator molecules via the 1,2-quinone carbonyl oxygen atoms. If this is the case, then a less than 1:1 molar ratio may be sufficient to achieve satisfactory stabilization.

Lithium salts have the advantage of the lowest molecular weights among those salts specified in embodiments of the invention such that a relatively low weight % is required to be added to the reagent formulation to achieve an approximate 1:1 molar ratio with the mediator. In contrast, the lanthanide metal salts may have up to approximately 7 to 8 times the molecular weight of lithium salts such that theoretically a very high weight % is required to achieve a 1:1 molar ratio. The lanthanide metal ions, however, have the capacity to bind more than 1 quinone mediator molecule.

In summary, the concentration of stabilizing metal salt must be optimised by experimentation for each individual metal ion and the selected redox mediator concentration while taking into account the theoretical ideal molar ratio of 1:1, the known coordination chemistry of the metal ion, and any other components of the reagent formulation including the enzyme which bind metal ions as guidance. Combinations of different metal ions listed in embodiments of the invention could be used.

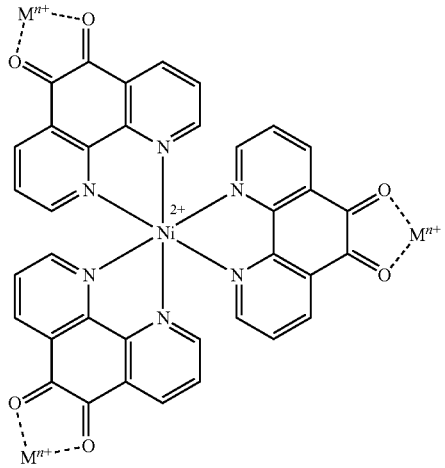

-continued

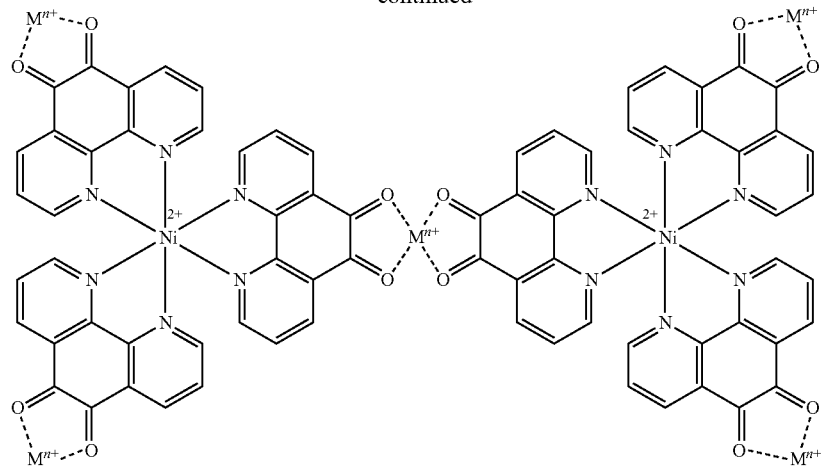

Provided above are two example modes of coordination of metal ions, $M^{n+}$, to the carbonyl oxygen atoms of a nickel complex of PQ for the purpose of inhibiting reaction with amines.

Response Stability

The issue of response stability at low glucose levels has been a recurring problem during the development of biosensor strip products containing PQ as a redox mediator. In particular, rising low glucose responses over time have been noted in some strip products. For certain strip products, those skilled in the art have improved stability at low glucose levels by reducing the amount of PQ redox mediator in the reagent formulation. A lower concentration of PQ creates fewer opportunities for amines present in the formulation to react with, and consequently reduce, the redox mediator.

For some biosensors, this work-around solution of lowering the level of the mediator is not an option. Newer biosensors, which employ a biamperometric system, require high levels of mediator. In these systems, the mediator is required to maintain optimum performance, especially at high glucose levels, at both the working and reference electrodes. This requirement exacerbates the low glucose stability issue because the high concentration of mediator creates greater opportunity for reaction with any amines present in the formulation.

The metal ions named in embodiments of the invention, particularly lithium, have been shown to stabilize newer biosensor formulations designed for biamperometric biosensor electrodes. The Examples presented herein will show that response stability in the absence of the above "stabilizing" metal ions is unacceptable.

The issue of low glucose stability is not confined to the PQ mediator system. For example, the use of ferrocyanide as a redox mediator has been reported whereby dicarboxylic acid buffers and cellulosic polymers are employed as stabilizers for this system (see, e.g., EP 1398386 and WO 2007/058999).

Figure 2:
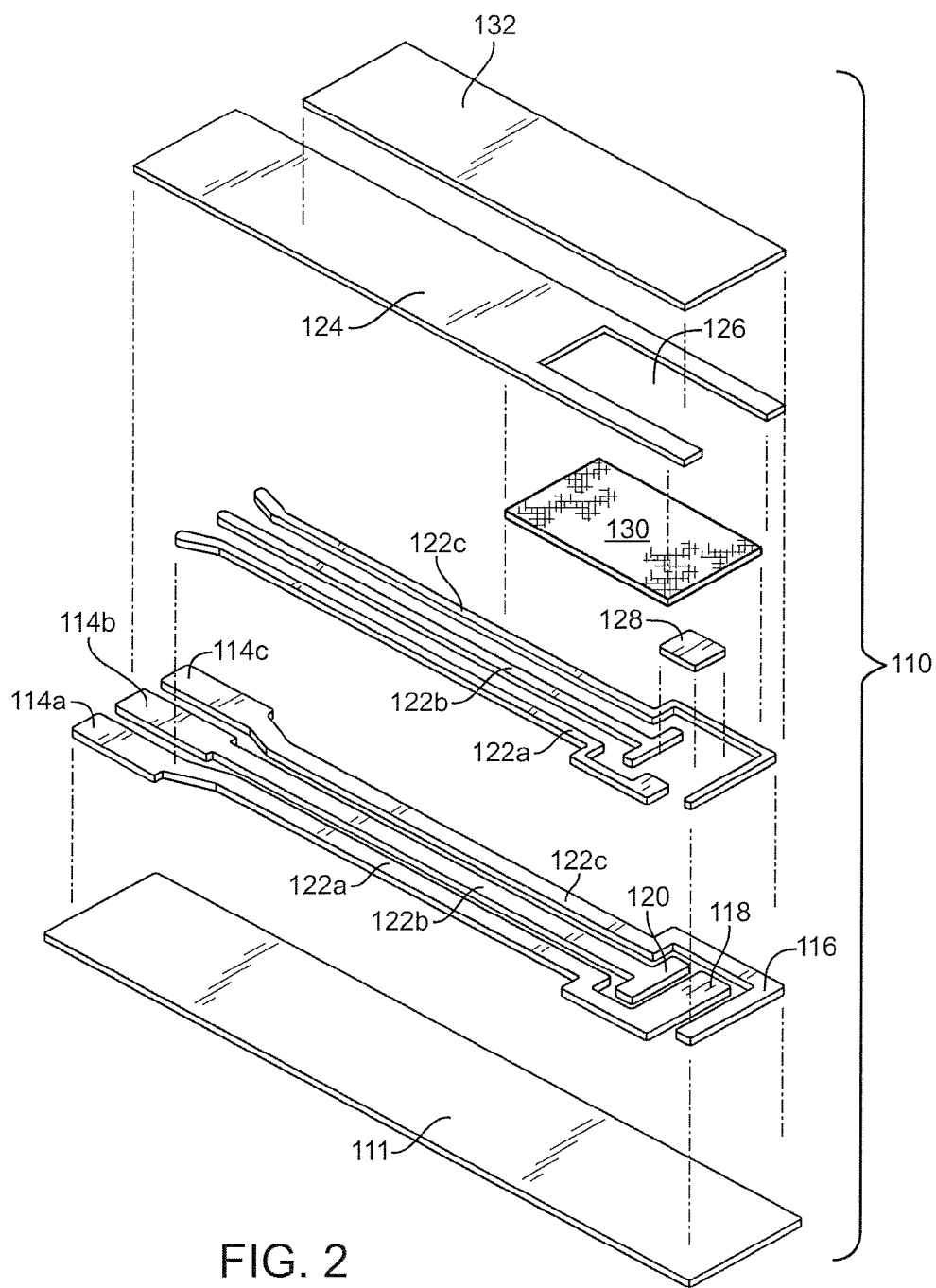
FIG. 2 is a schematic diagram that illustrates a perspective view of a standard amperometric strip with separate working and reference layers.
Figure 3:
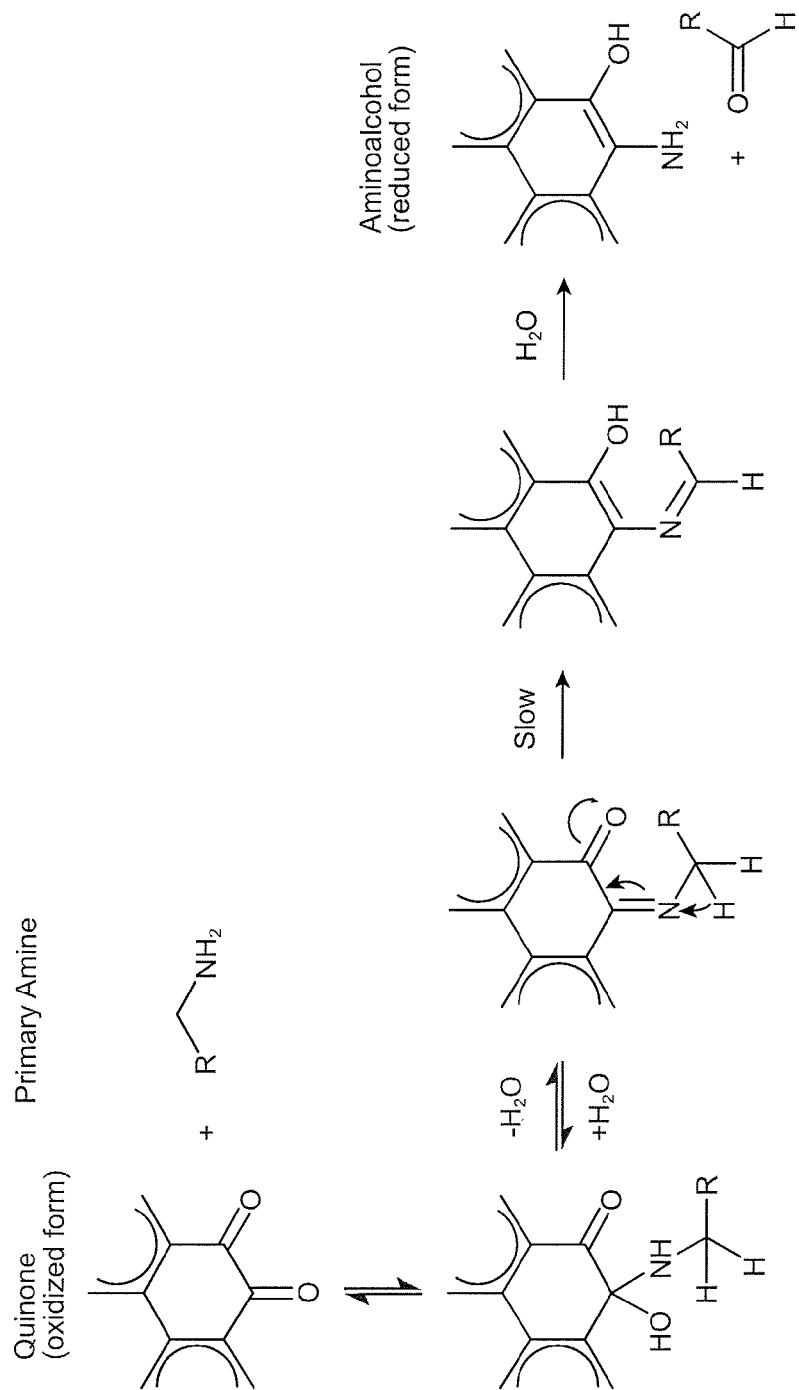
FIG. 3 illustrates the mechanism of reaction of a PQ-type quinone with a primary amine (e.g., lysine side-chain) leading to the formation of a reduced amino alcohol species.

Biosensor strips suitable for aspects of the invention are illustrated in FIGS. 1 and 2. Referring now to FIG. 1, a biamperometric strip 10 is shown having a combined working/reference layer. In a preferred embodiment, the strip comprises a patterned gold electrode substrate 12, e.g., a thin (~50 nm) gold layer deposited on an insulating polymer substrate, usually polyester (an electrode design or artwork of tracks and electrodes is then formed by removing gold in selected regions by such methods as laser ablation, chemical etching, etc.). The substrate 12 supports three tracks 14a, 14b, and 14c of electrically conductive gold. In another embodiment, the substrate 12 comprises only an insulating polymer substrate, usually polyester, and then an electrode design or artwork of tracks and electrodes is formed by printing a conducting ink, e.g., including carbon. The substrate 12 then supports three tracks 14a, 14b, and 14c of electrically conductive ink, e.g., including carbon. The tracks 14a, 14b, and 14c determine the positions of electrical contacts 16a, 16b, and 16c, a reference electrode 18, a working electrode 20, and a counter/start control electrode 22. The electrical contacts 16a, 16b, and 16c can be inserted into an appropriate measurement device (such as a meter receiving port) for measurement of current by making electrical contact with the internal electronics of a meter, for example.

Each of the elongated portions of the conductive tracks 14a, 14b, and 14c can optionally be overlaid with an opaque tape layer 24 which comprises a polymer film with an adhesive coating on the lower surface. The adhesive is preferably a pressure-sensitive adhesive (PSA). The upper surface may be decorated/printed with designs, logos, graphics, trademarks, identifiers, etc. Alternatively, the tape may be transparent and the decoration is printed on the lower surface, followed by an opaque printed layer, then finally the PSA layer. The prime function is as an insulator and protecting layer to prevent short-circuiting of the electrode tracks by biological sample and to protect the electrode tracks from damage, such as scratching.

Optionally, a cover layer 26 defining the upper boundary of the sample chamber for biological sample can overlay the opaque tape layer 24. The cover layer is made of a thin polymer tape, preferably polyester. The upper surface of the cover layer may be coated with a hydrophobic coating such that it is wetted poorly by the biological sample. The lower surface of the cover layer is coated with a hydrophilic coating, which may contain surfactants to promote filling of the biological sample into the sample chamber. The cover layer 26 is preferably transparent such that the progress of sample filling into the sample chamber can be monitored visually. This is a useful visual check that the sample chamber has filled completely.

A breather hole 28 functions to allow the release of air displaced from the sample chamber 30 by the ingress of biological sample. The sample chamber would not fill without this breather hole. The hole is preferably formed in the cover layer by the action of a laser and is aligned with the rear end of the sample chamber above the counter/start control electrode 22.

A spacer layer 32 comprises a thin (~100 μm) polymer tape layer with pressure-sensitive adhesive (PSA) on both surfaces. The spacer layer functions to define the dimensions (height and surface area) and shape of the sample chamber 30. The spacer layer confines the biological sample within the sample chamber and defines the area of the reagent layer 34 that is exposed to the biological sample. Optionally the spacer layer is colored to provide contrast between itself 32, the reagent layer 34 and the biological sample. In one embodiment, the spacer layer 32 and the cover 26 layer is contained within a pre-formed capillary sub-assembly and contains no mesh.

A reagent layer 34 comprises thin (~5 μm) film of active reagents (enzyme, redox mediator, cofactor), polymer film-former, additives, stabilizers, etc. Said reagent layer functions to act on the analyte of interest in the biological sample to provide a signal (proportional to the concentration of analyte) which translates to an electrical current in the electrode tracks. In one embodiment, said reagent layer 34 spans the whole width of the electrode strip covering all electrode tracks. A redox mediator may also be used as the reference redox couple for the reference electrode 18. In one embodiment, this layer is a combined working and reference layer.

A biological sample application/receiving area 36 may in one embodiment be a notch cut in the end of the electrode strip to identify to the user the point at which the biological sample should be applied. This receiving area 36 may also define the entrance to the sample chamber and promote ingress of the sample into the chamber.

The working electrode 20 includes a layer of conductive material containing a working area 20a. The working area 20a may be formed from a reagent composition, which is added (e.g., printed) on the layer of conductive material of the working electrode 20. The reagent composition includes a mixture of an oxidation-reduction mediator, a metal ion, a counter anion, an enzyme, and, optionally, a conductive material.

The working area 20 may be overlaid with reagent layer 34 derived from a printing ink or coating solution that includes the reagent composition described above, that includes a mixture of an enzyme, an oxidation-reduction mediator, a counter anion, a metal ion, and, optionally, a conductive material though short-circuits must be prevented. Alternatively, instead of an enzyme, the working area 20 can contain a substrate that is catalytically reactive with an enzyme to be assayed. The reagent composition is then applied in a single step to the working electrode area 20, counter electrode area 22 and the reference electrode area 18 as a single area of fixed length. In certain embodiments, the oxidation-reduction mediator comprises 1,10-phenanthroline-5,6-dione or $Ni(PQ)_3Cl_2$.

In other embodiments, the electrodes are formed on one or more electrode supports by any suitable method including chemical etching, laser ablation, photolithography, and the like. In general, the electrode support is formed from an insulating material, so that it will not provide an electrical connection between the electrodes of the electrode set. Examples include glass, ceramics and polymers. In certain embodiments, the electrode substrate is a flexible polymer, such as a polyester or polyimide.

For example, in the laser ablation process, the metallic layer may be ablated into an electrode pattern. Furthermore the patterned metallic layer may be coated or plated with additional metal layers. For example, the metallic layer may be copper, which is then ablated with a laser, into an electrode pattern; subsequently, the copper may be plated with a titanium/tungsten layer, and then a gold layer, to form the desired electrodes. In certain embodiments, however, only a single layer of gold is used, which is directly in contact with the electrode substrate. In such embodiments, the reagent composition can be positioned adjacent to the electrode(s).

In one such method, one or more channels are formed in the substrate, for example by an embossing process using an embossing die or roller. Other methods for forming the channels, such as the use of a laser, or photolithography and etching of the substrate can also be employed if desired.

The conductive material may contain pure metals or alloys, or other materials which are metallic conductors. Examples include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or metallic compounds of these elements. In certain embodiments, the conductive material includes carbon, gold, platinum, palladium, iridium, or alloys of these metals, since such noble metals and their alloys are unreactive in biological systems.

The reagent composition includes an aqueous solution of, a redox mediator, a coordinating metal ion and its counter anion, as well as a stabilizing metal ion and its counter anion. For the working electrode 20, the reagent composition also includes an enzyme. For example, when the analyte to be measured is glucose in blood, the enzyme is glucose dehydrogenase, and the redox mediator is a 1,10-phenanthroline-5,6-dione. In the alternative, for the working electrode 20, the printing ink can include a substrate in lieu of an enzyme when the analyte to be measured is an enzyme.

In certain embodiments, the reagent composition can be screen-printed. In such embodiments, the reagent composition can further include a polysaccharide (e.g., a guar gum or an alginate), a hydrolyzed gelatin, an enzyme stabilizer (e.g., glutamate or trehalose), a film-forming polymer (e.g., a polyvinyl alcohol), a defoaming agent, a buffer, or a combination of the foregoing.

The electrodes cannot be spaced so far apart that the working electrode 20, the counter electrode 22 and the reference electrode 18 cannot be covered by the sample. In certain embodiments, the length of the path to be traversed by the sample (i.e., the sample path) is kept as short as possible in order to minimize the volume of sample required. The maximum length of the sample path can be as great as the length of the biosensor strip. However, the corresponding increase in resistance of the sample limits the length of the sample path to a distance that allows the necessary response current to be generated. The resistance of the sample is also influenced by the distance from the edge of the area of the reference electrode 18 and counter electrode 22 to the edge of the working area of the working electrode 20. Positioning the electrodes contiguously is conventional.

The counter/start control electrode 22 can be placed downstream of the reference electrode. The counter/start control electrode 22 can be used to determine when the sample has been applied to the strip, thereby activating the assay protocol. See, e.g., U.S. Ser. No. 09/529,617, filed Jun. 7, 2000, now U.S. Pat. No. 6,736,957, the disclosure of which is incorporated herein by reference in its entirety.

A standard amperometric strip 110 with separate working and reference layers suitable for aspects of the invention is illustrated in FIG. 2. Referring now to FIG. 2, an electrode support 111, such as an elongated strip of polymeric material (e.g., polyvinyl chloride, polycarbonate, polyester, or the like) supports three tracks 112a, 112b, and 112c of electrically conductive ink, such as carbon. These tracks 112a, 112b, and 112c determine the positions of electrical contacts 114a, 114b, and 114c, a reference electrode 116, a working electrode 118, and a counter electrode 120. The electrical contacts 114a, 114b, and 114c are insertable into an appropriate measurement device (not shown) for measurement of current.

Each of the elongated portions of the conductive tracks 112a, 112b, and 112c can optionally be overlaid with a track 122a, 122b, and 122c of conductive material, for example made of a mixture including silver particles and silver chloride particles. The enlarged exposed area of track 122b overlies the reference electrode 116. A layer of a hydrophobic electrically insulating material 124 further overlies the tracks 112a, 112b, and 112c. The positions of the reference electrode 116, the working electrode 118, the counter electrode 120, and the electrical contacts 114a, 114b, and 114c are not covered by the layer of hydrophobic electrically insulating material 124. This hydrophobic electrically insulating material 124 serves to prevent short circuits. The layer of hydrophobic electrically insulating material 124 has an end-fill opening 126 formed therein. This opening 126 provides the boundary for the reaction zone of the biosensor strip 110. Because this insulating material is hydrophobic, it can cause the sample to be restricted to the portions of the electrodes in the reaction zone. The working electrode 118 comprises a layer of a non-reactive electrically conductive material on which is deposited a layer 128 containing a reagent composition for carrying out an oxidation-reduction reaction. At least one layer of mesh 130 overlies the electrodes. This layer of mesh 130 protects the printed components from physical damage. The layer of mesh 130 also helps the sample to wet the electrodes by reducing the surface tension of the sample, thereby allowing it to spread evenly over the electrodes. A cover 132 encloses the surfaces of the electrodes that are not in contact with the electrode support 111. This cover 132 is a liquid impermeable membrane.

The reagent composition 128 is deposited on that portion of the electrically conductive material of the working electrode 118 where the oxidation-reduction reaction is to take place when a sample is introduced to the biosensor strip 110. In such embodiments, the reagent composition 128 can be applied to the working electrode 118 as a discrete area having a fixed length. Typical analytes of interest include, for example, glucose and ketone bodies. Typical non-reactive electrically conductive materials include, for example, carbon, platinum, palladium, iridium, and gold. A semiconducting material such as indium doped tin oxide can be used as the non-reactive electrically conductive material. In certain embodiments, the reagent composition includes a mixture of an oxidation-reduction mediator and an enzyme. Alternatively, instead of an enzyme, the reagent composition can contain a substrate that is catalytically reactive with an enzyme to be assayed. In the biosensor strips of aspects of the invention, the reagent(s) are applied in the form of a composition containing particulate material and having binder(s), and, accordingly, does not dissolve rapidly when subjected to the sample. In view of this feature, the oxidation-reduction reaction will occur at the interface of working electrode 118 and the sample. The glucose molecules diffuse to the surface of the working electrode 118 and react with the enzyme/mediator mixture.

In addition to being applied to the working electrode 118, a layer of the reagent composition can be applied to any of the other electrodes, such as the reference electrode when desired, as a discrete area having a fixed length.

Other possible biosensor strip designs include those in which the mesh layer 130 is eliminated, and the flow channel is of such dimensions that the biosensor strip takes up a liquid sample by capillary attraction. See U.S. Ser. No. 10/062,313, filed Feb. 1, 2002, incorporated herein by reference.

The mediator can be used for any $NAD(P)^+$ dependent enzyme. Representative examples of these enzymes are set forth in Table 1.

TABLE 1

| E.C. (enzyme classification) Number | Enzyme name |
|---|---|
| 1.1.1.1 | Alcohol dehydrogenase |
| 1.1.1.27 | Lactate dehydrogenase |
| 1.1.1.31 | β-hydroxybutyrate dehydrogenase |
| 1.1.1.49 | Glucose-6-phosphate dehydrogenase |
| 1.1.1.47 | Glucose dehydrogenase |
| 1.2.1.46 | Formaldehyde dehydrogenase |
| 1.1.1.37 | Malate dehydrogenase |
| 1.1.1.209 | 3-hydroxysteroid dehydrogenase |

Other enzyme systems that can be used with the mediator include, but are not limited to, oxidases (glucose oxidase, cholesterol oxidase, lactate oxidase) and FAD-GDH. Formulations for screen-printing reagents on an electrode comprise the components set forth in Table 2 and Table 3, where % means % by weight.

TABLE 2

| | |
|---|---|
| $(NAD)P^+$ dependent enzyme (such as glucose dehydrogenase) | 200 to 4000 units per gram |
| Nicotinamide adenine dinucleotide (NAD) | 5 to 30% |
| 1,10-phenanthroline-5,6-dione | 0.1 to 1.5% |
| Filler (such as carbon or silica) | 10 to 30% |
| Binder (such as hydroxyethyl cellulose or guar gum or alginate) | 0.01 to 0.5% |
| Protein stabilizer (such as trehalose or bovine serum albumin) | 0.01 to 2% |
| Metal ion | 0.1 to 10% |
| Buffers and other electrolytes | 1 to 10% |

TABLE 3

| | |
|---|---|
| $(NAD)P^+$ dependent enzyme (such as glucose dehydrogenase) | 200 to 4000 units per gram |
| Nicotinamide adenine dinucleotide (NAD) | 5 to 30% |
| Metal complex of 1,10-phenanthroline-5,6-dione | 0.1 to 1.5% |
| Filler (such as carbon or silica) | 10 to 30% |
| Binder (such as hydroxyethyl cellulose or guar gum or alginate) | 0.01 to 0.5% |
| Protein stabilizer (such as trehalose or bovine serum albumin) | 0.01 to 15% |
| Buffers and other electrolytes | 1 to 10% |

The performance of biosensors for determining electrochemical ketone bodies can also be enhanced with the use of this chemistry. A typical formulation for determination of ketone bodies is shown in Table 4.

TABLE 4

| | |
|---|---|
| β-hydroxybutyrate dehydrogenase | 200 to 4000 units per gram |
| Nicotinamide adenine dinucleotide (NAD) | 5 to 30% |

TABLE 4-continued

| | |
|---|---|
| 1,10-phenanthroline-5,6-dione | 0.1 to 1.5% |
| Filler (such as carbon or silica) | 10 to 30% |
| Binder (such as hydroxyethyl cellulose or guar gum or alginate) | 0.01 to 0.5% |
| Protein stabilizer (such as trehalose or bovine serum albumin) | 0.01 to 2% |
| Metal ion | 0.1 to 10% |
| Buffers and other electrolytes | 1 to 10% |

In general, NAD(P)$^+$-dependent enzymes react with substrate according to the relationship:

$$RH_2 + NAD(P)^+ \rightarrow R + NAD(P)H + H^+$$

NAD(P)H is oxidized back to NAD(P)$^+$ by the mediator described in embodiments of the invention. The rate of this oxidation reaction is slower than that of other isomers (1,7-phenanthroline-5,6-dione and 4,7-phenanthroline-5,6-dione). This slow reaction rate prevents rapid regeneration of the coenzyme and hence makes it susceptible to variation in hematocrit or oxygen in the sample. The mediator will have higher probability of reacting with molecular oxygen and hence become sensitive to oxygen. The diffusion of the mediator in the sample is affected by the hematocrit variation and slow reacting mediator will be more affected by restricted mobility compared to a fast reacting mediator. The metal ions described herein allow rapid regeneration of the coenzyme and hence make the co-enzyme less susceptible to variation in hematocrit or oxygen in the sample.

EXPERIMENTAL

The following examples are put forth so as to provide those of ordinary skill in the art with a complete disclosure and description of how to make and use aspects and embodiments of the present invention, and are not intended to limit the scope of what the inventors regard as the claimed subject matter nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Figure 14:
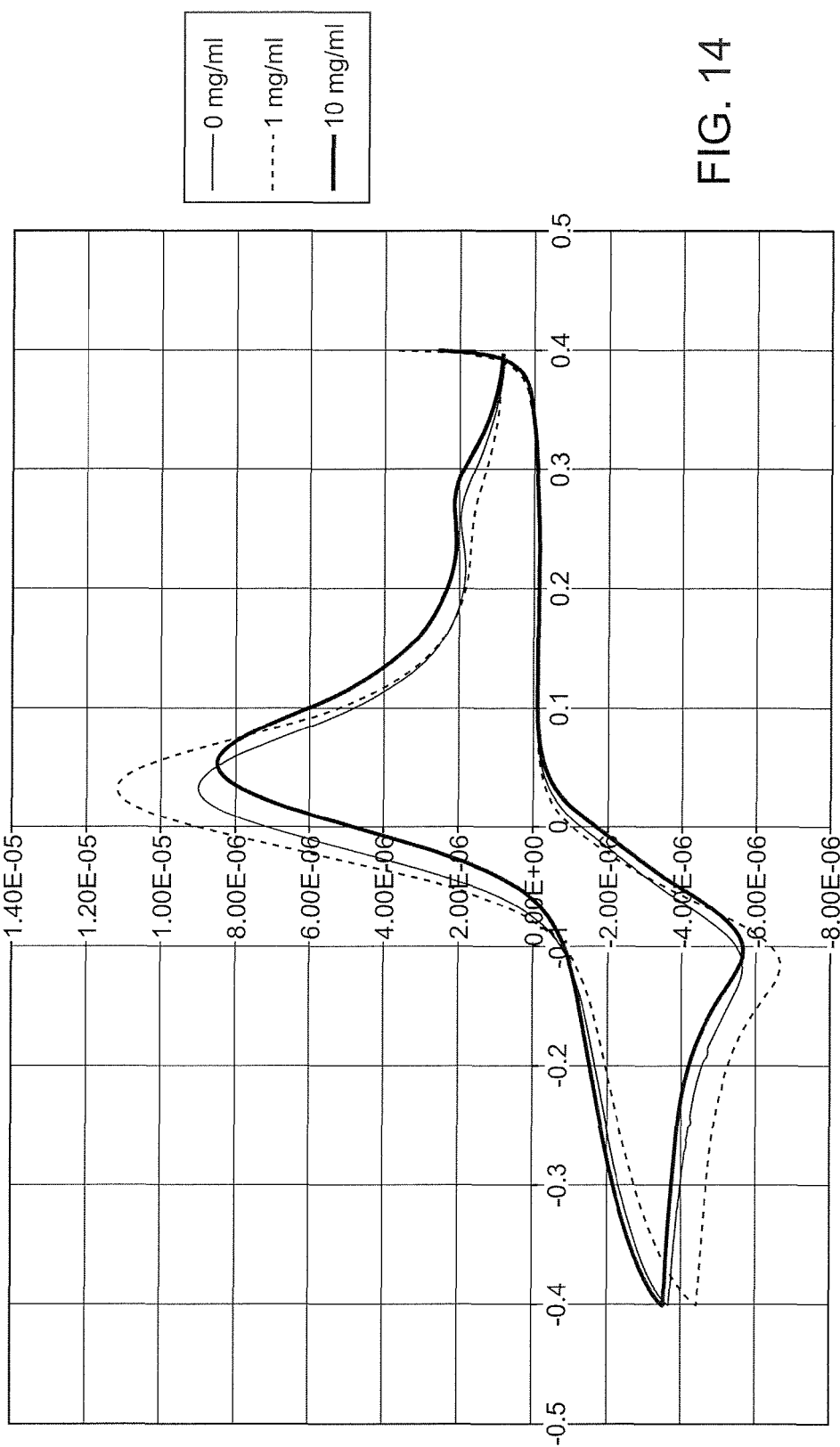
FIG. 14-16 are a cyclic voltammograms (x-axis: potential in units of V; y-axis: current in units of A) that illustrate the effects of lithium chloride (FIG. 14), magnesium chloride (FIG. 15), and scandium triflate (FIG. 16) on the electrochemistry of $Ni(PQ)_3Cl_2$.
Figure 15:
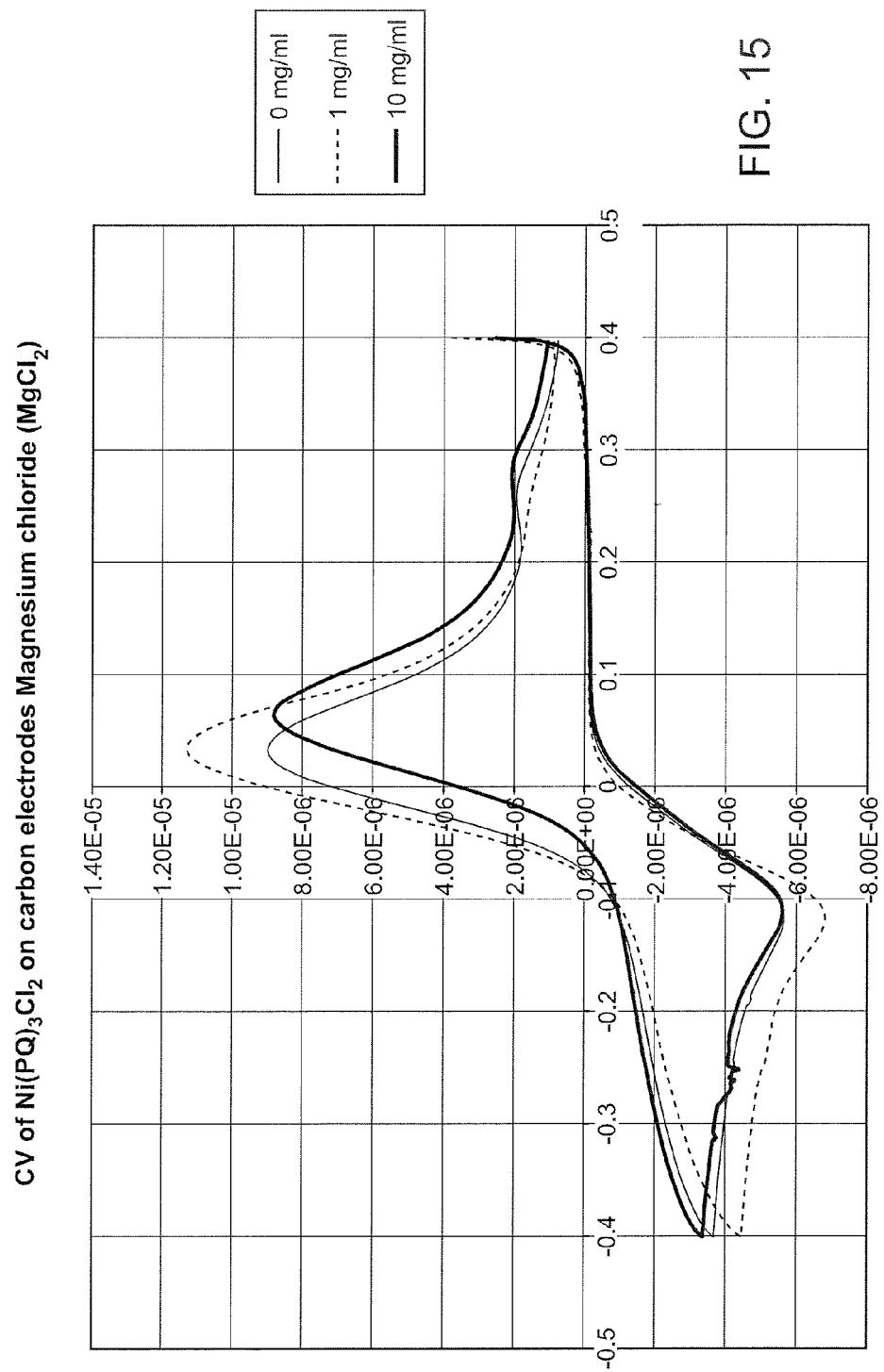
Figure 16:
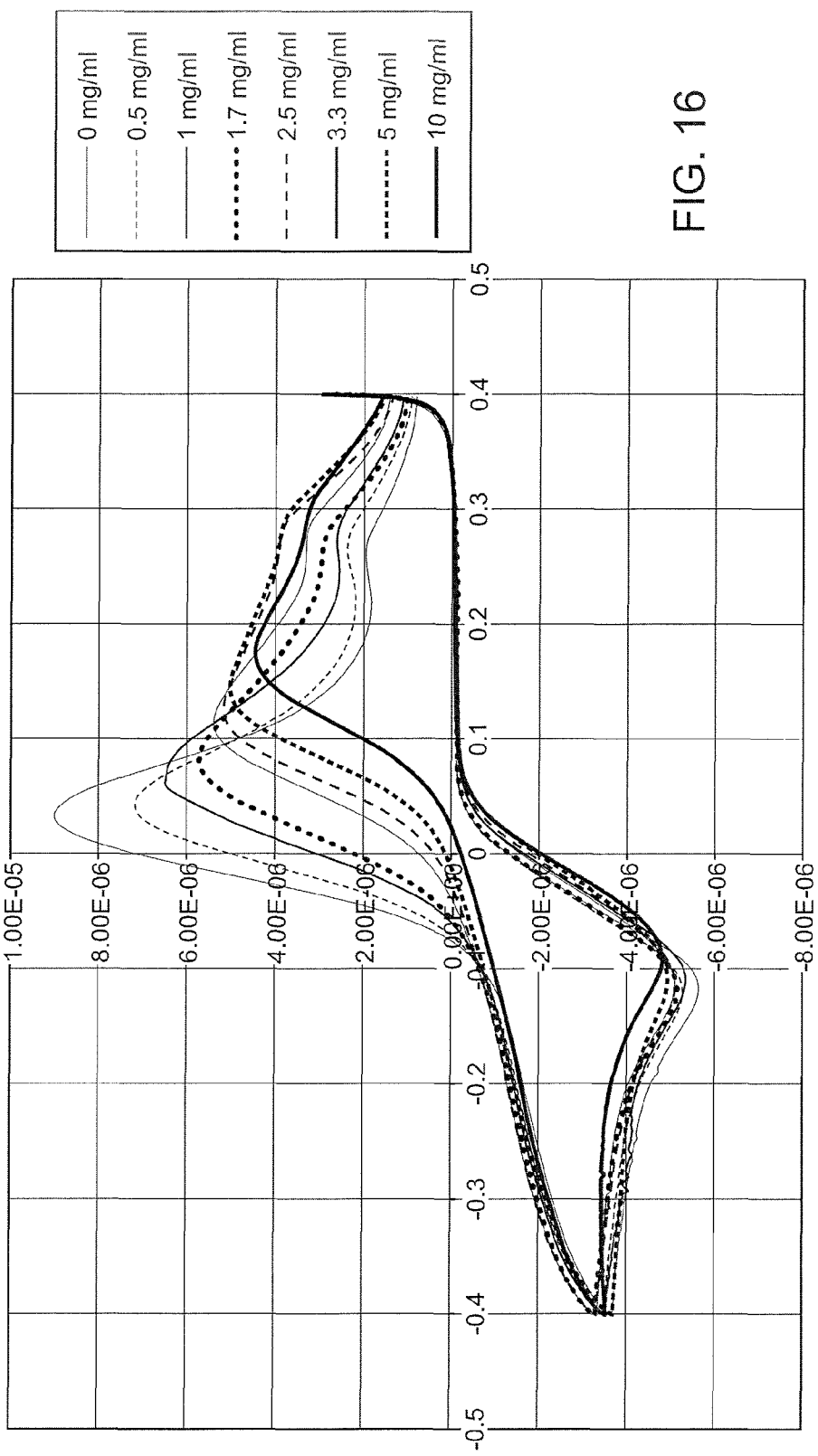

A. Effect of Various Metal Ions on the Electrochemistry of the Redox Mediator Ni(PQ)$_3$Cl$_2$ in Aqueous Solution Solutions of Ni(PQ)$_3$Cl$_2$ (1 mM) in PBS in the presence of various metal ions at different concentrations in the range 0-10 mg/ml were prepared. The solutions were applied using a volume of 10 µl to screen-printed carbon electrodes of the type depicted in FIG. 2 with the cover 132 removed. Cyclic voltammograms (CV) of these solutions were then recorded by scanning from +0.4 V (versus Ag/AgCl) to −0.4 V then back to +0.4 V at a scan rate of 50 mV/s. The cyclic voltammograms (x-axis: potential in units of V; y-axis: current in units of A) shown in FIGS. 14-16 illustrate the effect of lithium chloride (FIG. 14), magnesium chloride (FIG. 15), and scandium triflate (FIG. 16) on the electrochemistry of Ni(PQ)$_3$Cl$_2$. Generally, only a very small positive shift in the oxidation potential (E$_{ox}$) of Ni(PQ)$_3$Cl$_2$ is observed. It is noted that the magnitude of the E$_{ox}$ depends on the identity and concentration of the metal ion. There is no shift in the reduction potential of Ni(PQ)$_3$Cl$_2$ induced by the presence of the metal ions. In contrast, a literature article (Yuasa et al. (2006) *Chem. Phys. Chem.* 7:942-954) has reported that the reduction potential (E$_{red}$) of PQ in acetonitrile solution is strongly shifted in a positive direction in the presence of metal ions. Table 5 below summarizes the measured shifts in E$_{ox}$ of Ni(PQ)$_3$Cl$_2$ in aqueous solution caused by the various metal ions of this invention. It can be seen that scandium and the lanthanide metal ions have the largest effect on the E$_{ox}$ of Ni(PQ)$_3$Cl$_2$ but that this effect is only significant at very high concentrations (>20 mM versus 1 mM for the Ni complex) above those which would be reasonably used in this invention. For these metal ions, the shift in Eox is less than 50 mV at low concentrations comparable to that of the redox mediator.

TABLE 5

Effect of metal ions on the oxidation potential (E$_{ox}$) of Ni(PQ)$_3$Cl$_2$ in aqueous solution (1 mM)

| | 1 mg/ml metal salt | | 10 mg/ml metal salt | |
|---|---|---|---|---|
| Metal salt | Concentration (mM) | Shift in E$_{ox}$ (mV) | Concentration (mM) | Shift in E$_{ox}$ (mV) |
| LiCl | 23.6 | 0 | 236 | 20 |
| NaCl | 17.1 | 0 | 171 | 27 |
| KCl | 13.4 | 0 | 134 | 22 |
| RbCl | 8.27 | 0 | 82.7 | 10 |
| CsCl | 5.94 | 0 | 59.4 | 12 |
| NH$_4$Cl | 18.7 | 0 | 187 | 24 |
| MgCl$_2$ | 10.5 | 0 | 105 | 32 |
| CaCl$_2$•6H$_2$O | 4.56 | 5 | 45.6 | 54 |
| SrCl$_2$•6H$_2$O | 3.75 | 7 | 37.5 | 34 |
| BaCl$_2$•6H$_2$O | 4.09 | 17 | 40.9 | 58 |
| ScTf$_3$ (Tf = triflate) | 2.03 | 37 | 20.3 | 142 |
| LaCl$_3$•7H$_2$O | 4.08 | 24 | 40.8 | Obscured |
| CeCl$_3$•7H$_2$O | 2.68 | 39 | 26.8 | 195 |
| SmCl$_3$•6H$_2$O | 2.74 | 46 | 27.4 | 212 |
| EuCl$_3$•6H$_2$O | 2.73 | 46 | 27.3 | 173 |
| HoCl$_3$•6H$_2$O | 2.64 | 44 | 26.4 | 215 |
| LuCl$_3$•6H$_2$O | 2.57 | 20 | 25.7 | 171 |

B. Preparation of Electrodes with Reagent Film for Accelerated Stability Studies A stock aqueous reagent coating solution was prepared containing: 3.4% [Ni(PQ)$_3$]Cl$_2$/2% polymer/5% trehalose/2% NAD-dependent glucose dehydrogenase (NAD-GDH)/0.5% NAD or 3.4% [Ni(PQ)$_3$]Cl$_2$/2% polymer/5% trehalose/1.3% FAD-dependent glucose dehydrogenase (FAD-GDH).

Various metal salts were then added, usually at a level of 0.7%, and the resulting solution was used to coat gold electrodes by hand- or via slot-coating. Coated electrodes were dried for 3 min at 75° C. Pre-formed capillary fill cells were then applied and the strips trimmed to size. The resulting electrodes were stored in sealed desiccated pots at 50° C. or 75° C. for the purpose of accelerated ageing to test the effectiveness of various metal salts as stabilizers. Testing was with either (a) the appropriate substrate/analyte (usually glucose) control solutions or (b) phosphate buffered saline solution (PBS) containing no substrate (0 mM). Test parameters were: 1 sec delay, +200 mV applied potential (vs. mediator redox couple-biamperometry), 100 Hz sampling time, manual assay start. For glucose calibrations, the mean integrated current was recorded between 2.5 and 3.0 secs. For background testing (0 mM) with PBS, the current at 1.0 sec was recorded for the purpose of comparing.

Working: Ni(PQ)$_3$+NADH=Ni(PQH$_2$)$_3$+NAD then Ni(PQH$_2$)$_3$ is oxidized to Ni(PQ)$_3$ at the electrode.

Figure 4:
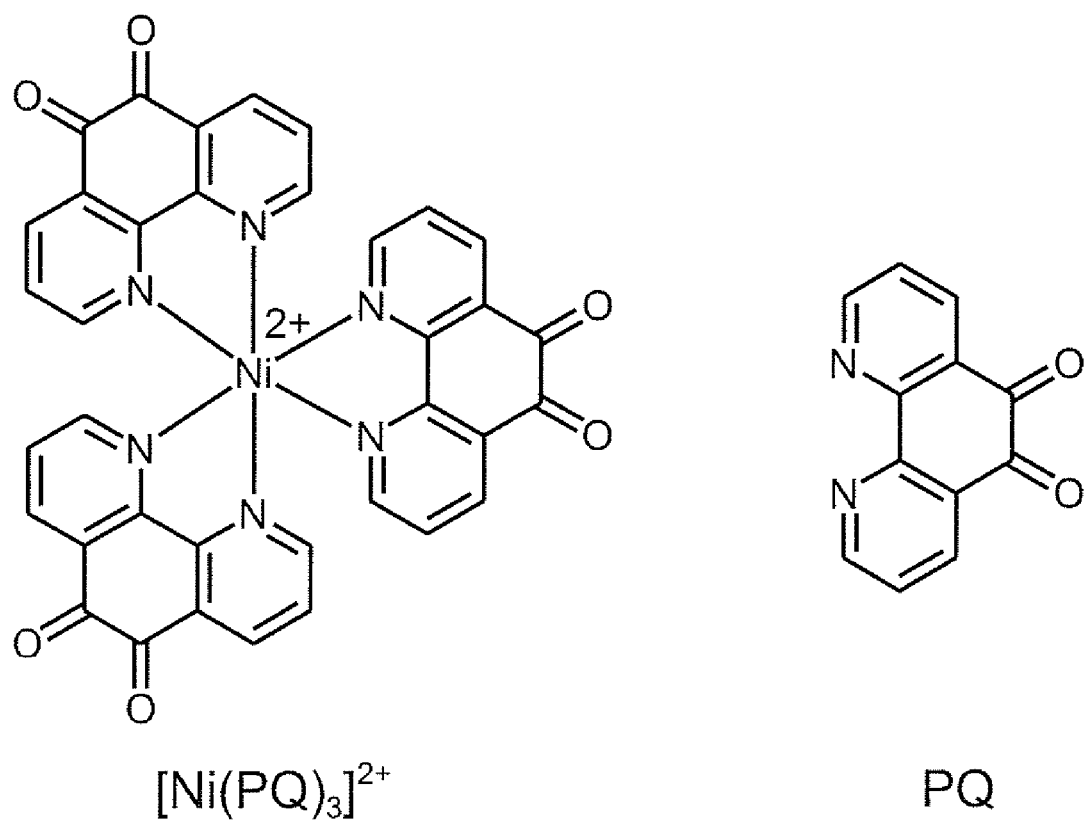
FIG. 4 illustrates a transition metal complex of 1,10-phenanthroline quinone (PQ) and nickel ion ($Ni^{2+}$) and a single PQ species.

Ref/counter: Ni(PQ)3 is reduced to Ni(PQH2) at the electrode. The hand fabrication of coated gold electrodes is depicted in FIG. 4.

Figure 5:
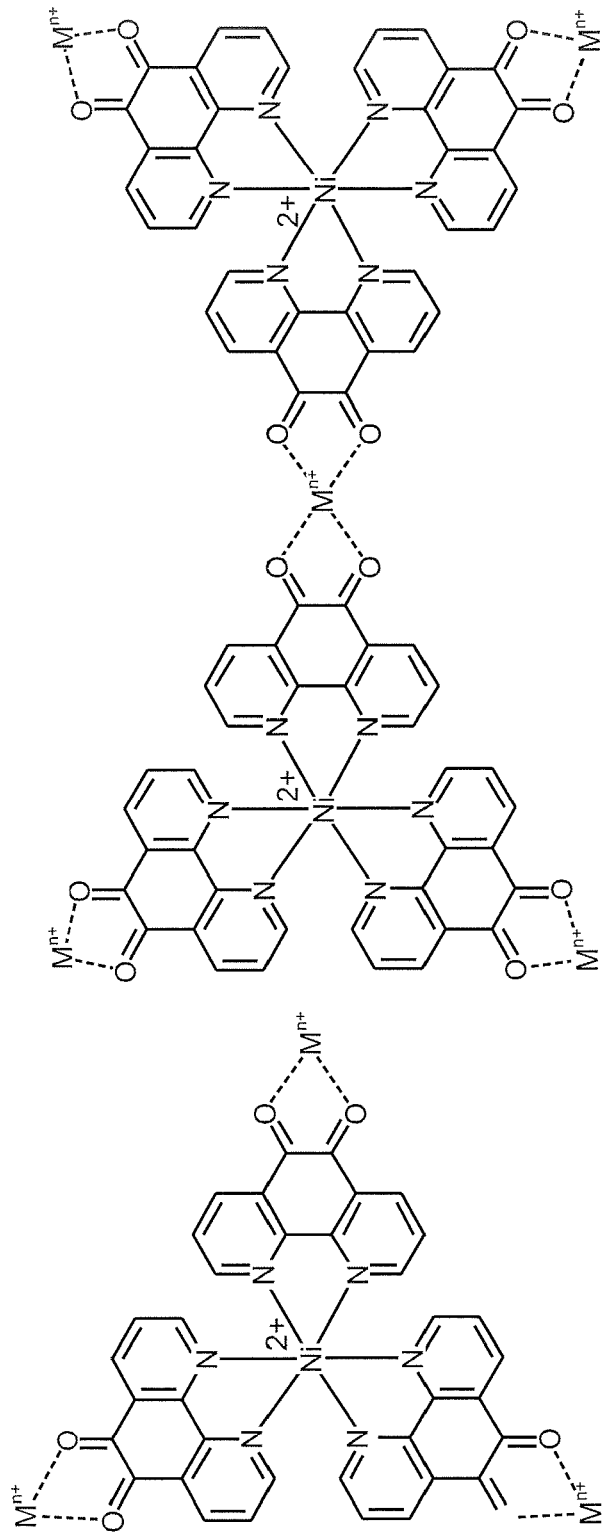
FIG. 5 illustrates two example modes of coordination of metal ions, $M^{n+}$, to the carbonyl oxygen atoms of a nickel complex of PQ for the purpose of inhibiting reaction with amines.
Figure 6:
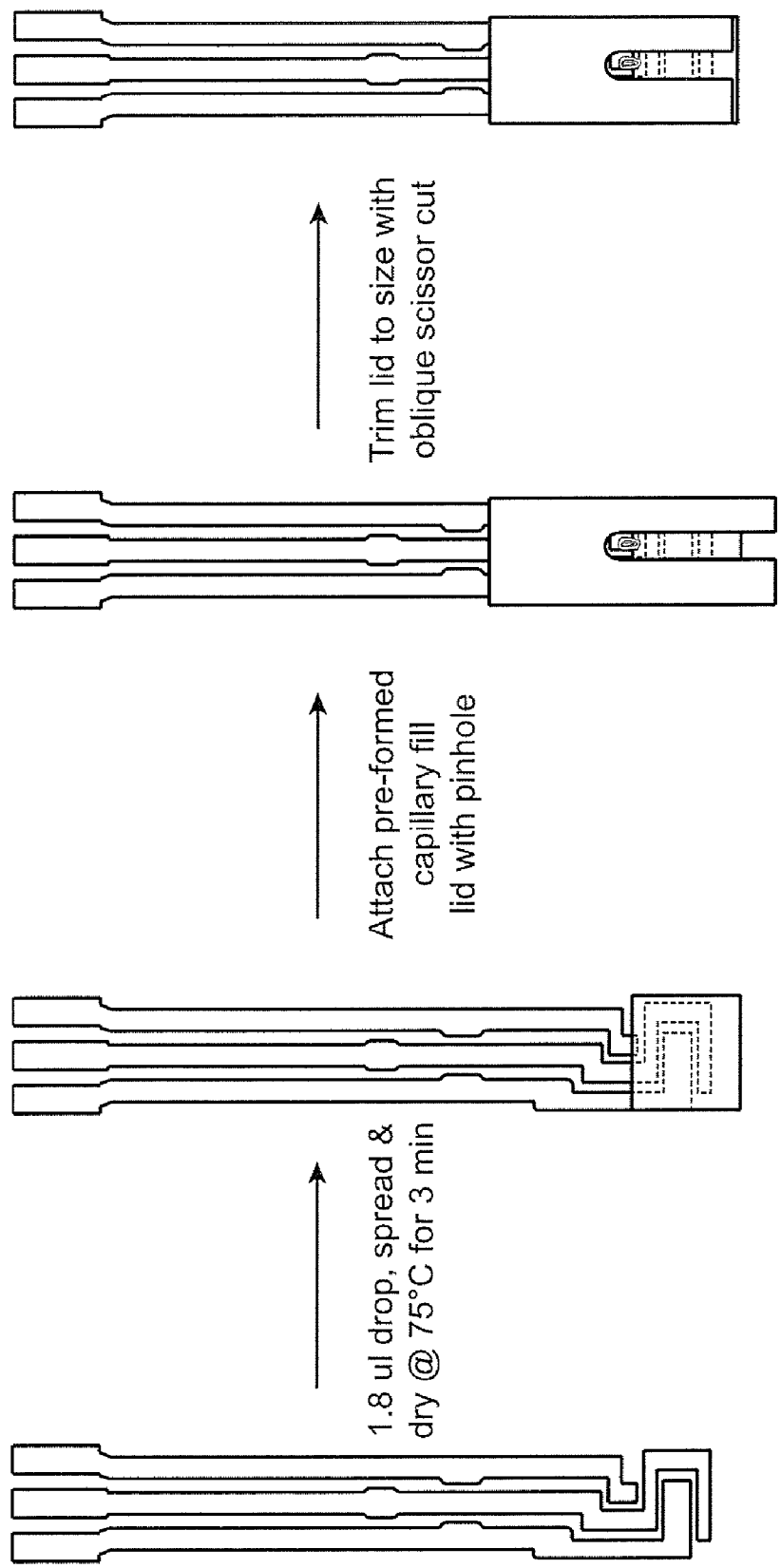
FIG. 6 illustrates the hand fabrication of coated gold electrodes.
Figure 7:
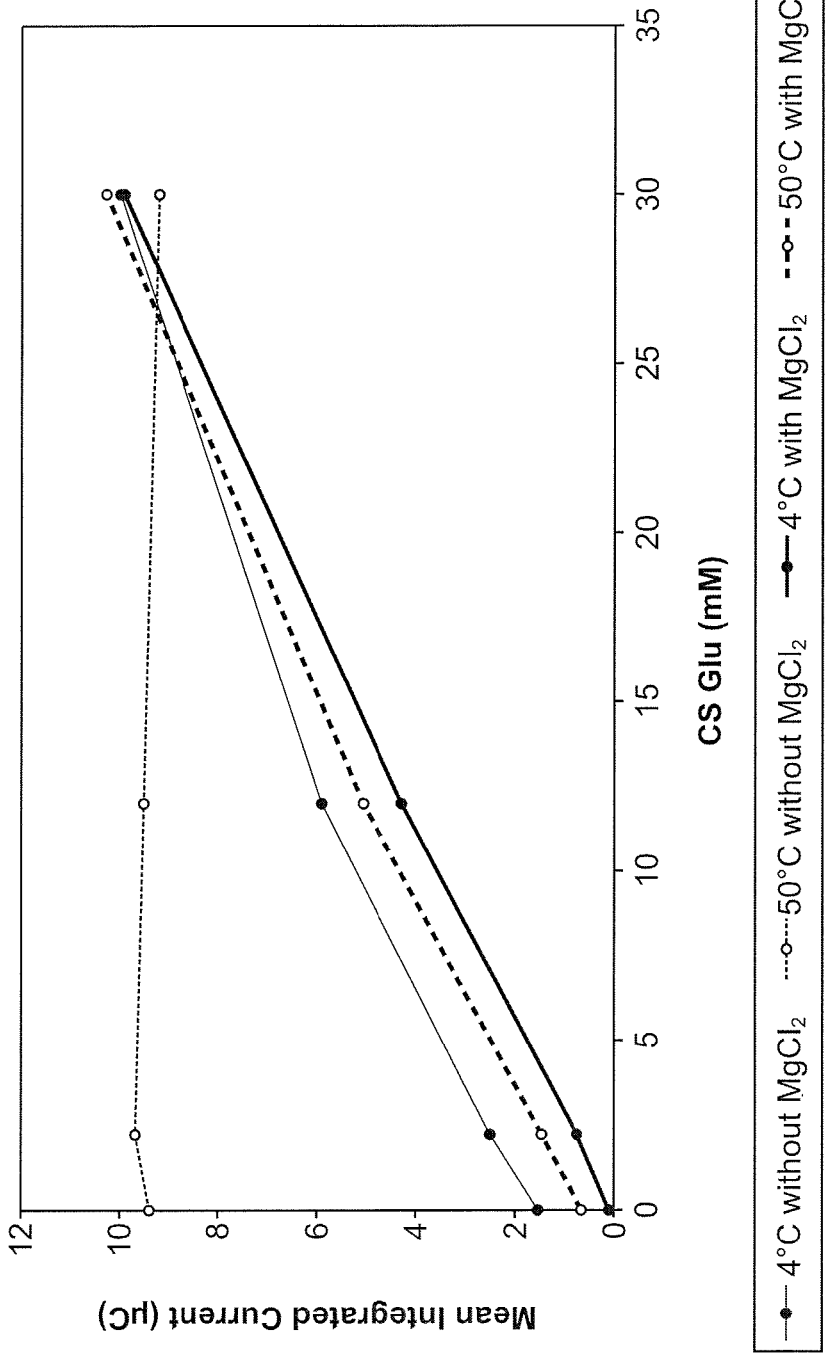
FIG. 7 illustrates the glucose calibration plots resulting from a comparison of electrode stability at 50° C. with and without magnesium chloride as a stabilizer. The electrodes contain NAD-GDH as the enzyme. The batch containing no magnesium chloride is clearly unstable at 50° C., the instability manifesting itself as a rise in low-end response over time such that it is comparable to the high-end response after 4 weeks, i.e., there is a high background signal with no response to different glucose concentrations. In contrast, the batch containing 0.7% magnesium chloride displays only a slightly elevated response to glucose for the electrodes stored at 50° C. compared to those stored at 4° C.

C. Comparison of Electrode Stability at 50° C., with and without Magnesium Chloride as a Stabilizer, NAD-GDH Enzyme Two batches of coated gold electrodes were prepared using identical formulations (see above) except for the presence of 0.7% magnesium chloride in one. The two batches were then stored at 4° C. and 50° C. for 4 weeks before being tested for response to glucose. FIG. 5 displays the resulting glucose calibration plots. The batch containing no magnesium chloride is clearly unstable at 50° C., the instability manifesting itself as a rise in low-end response over time such that it is comparable to the high-end response after 4 weeks, i.e., there is a high background signal with no response to different glucose concentrations. In contrast, the batch containing 0.7% magnesium chloride displays only a slightly elevated response to glucose for the electrodes stored at 50° C. compared to those stored at 4° C.

D. Reconstitution of Screening of Various Metal Salts as Stabilizers in Electrodes Containing NAD-GDH and FAD-GDH Stored at 75° C.

Several batches of electrodes were coated with formulations containing 0.7% of various metal salts. The resulting electrodes were stored at 75° C. for a period of days before being tested with PBS for 0 mM background response at 1 sec.

Figure 8:
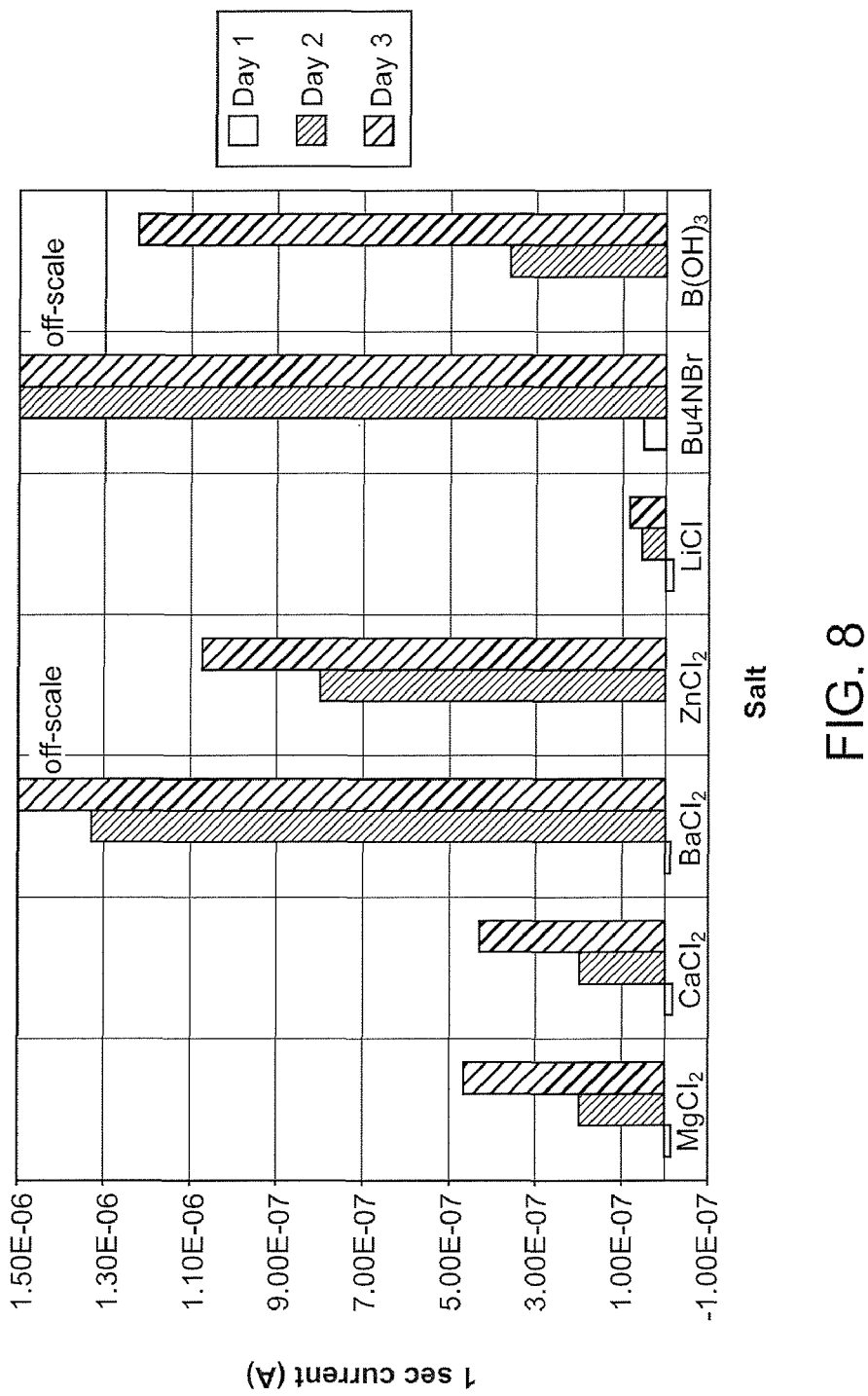
FIG. 8 illustrates that magnesium, calcium and lithium ions are effective stabilizing ions in the NAD-GDH system compared to barium, zinc, tetrabutylammonium and borate. Strip containing lithium ions had the lowest background response and hence were the most effective stabilizer.

FIG. 8 shows that magnesium, calcium and lithium ions are effective stabilizing ions in the NAD-GDH system compared to barium, zinc, tetrabutylammonium and borate. Strip containing lithium ions had the lowest background response and hence were the most effective stabilizer.

Figure 9:
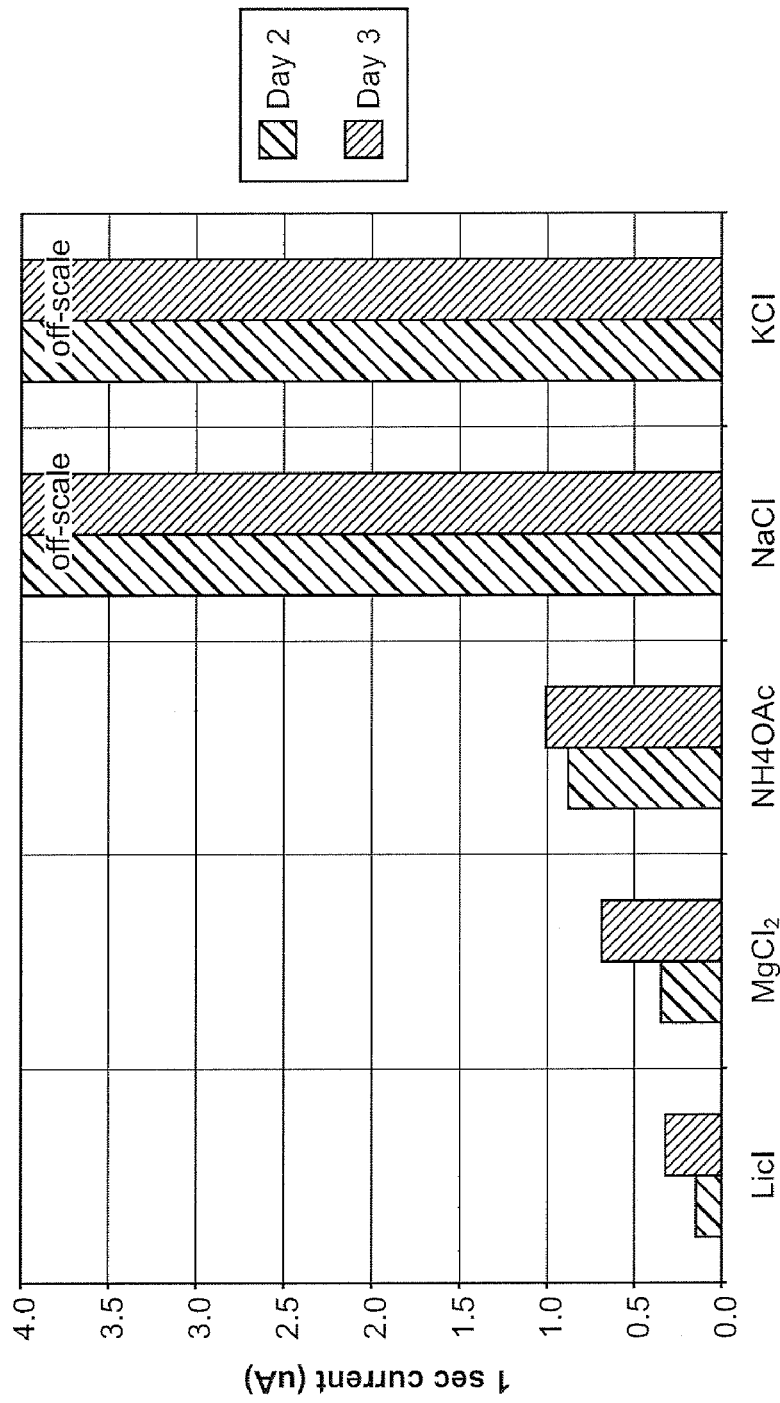
FIG. 9 illustrates that sodium and potassium ions have no stabilizing effect in the NAD-GDH system in comparison to lithium and magnesium ions. Again, lithium ions had the biggest stabilizing effect.

FIG. 9 shows that sodium and potassium ions have no stabilizing effect in the NAD-GDH system in comparison to lithium and magnesium ions. Again, lithium ions had the biggest stabilizing effect.

Figure 10:
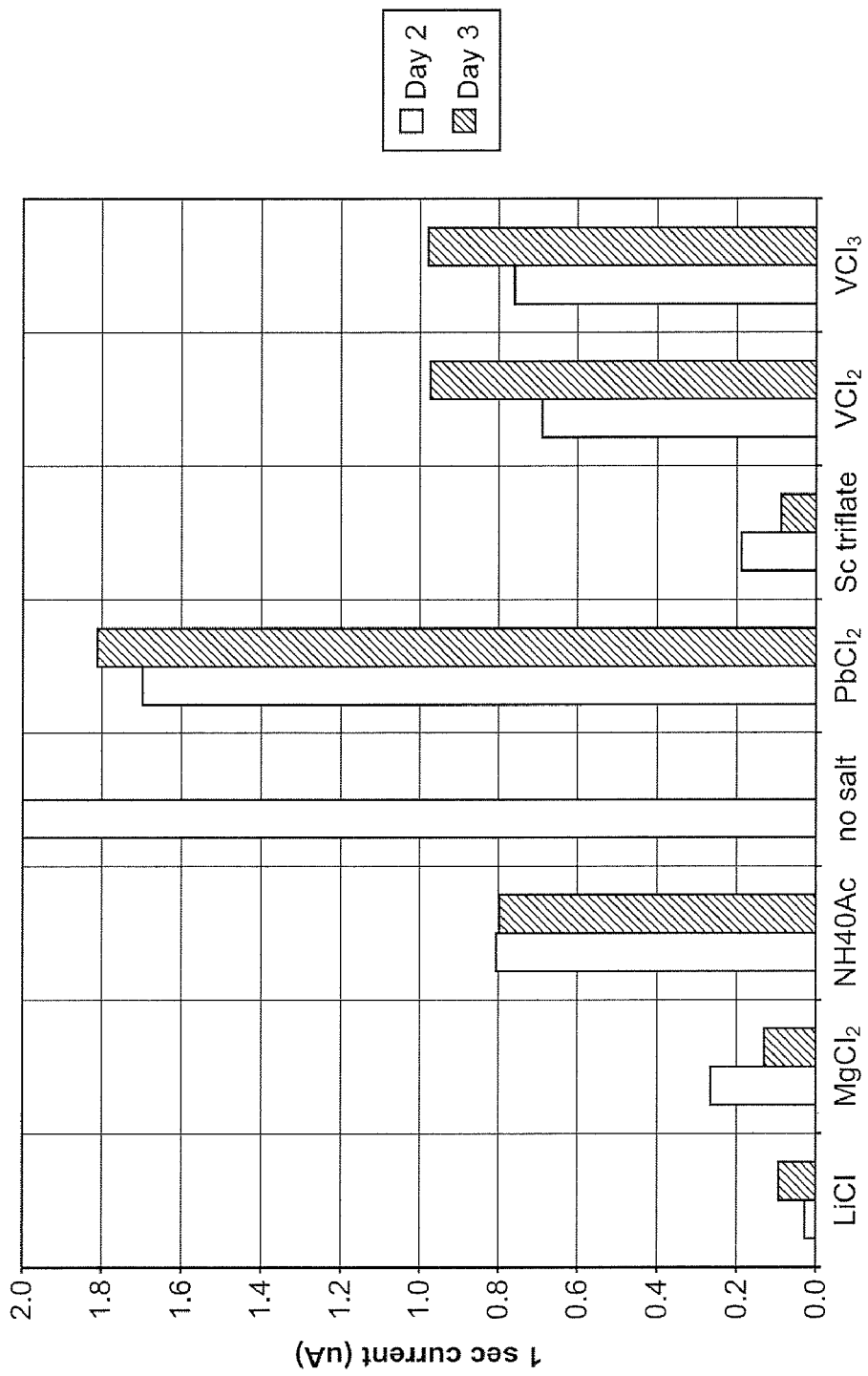
FIG. 10 illustrates that scandium ions have a good stabilizing effect in the NAD-GDH system comparable to lithium and magnesium while lead, vanadium were poor. Again, lithium was the best stabilizing ion.

FIG. 10 shows that scandium ions have a good stabilizing effect in the NAD-GDH system comparable to lithium and magnesium while lead, vanadium were poor. Again, lithium was the best stabilizing ion.

Figure 11:
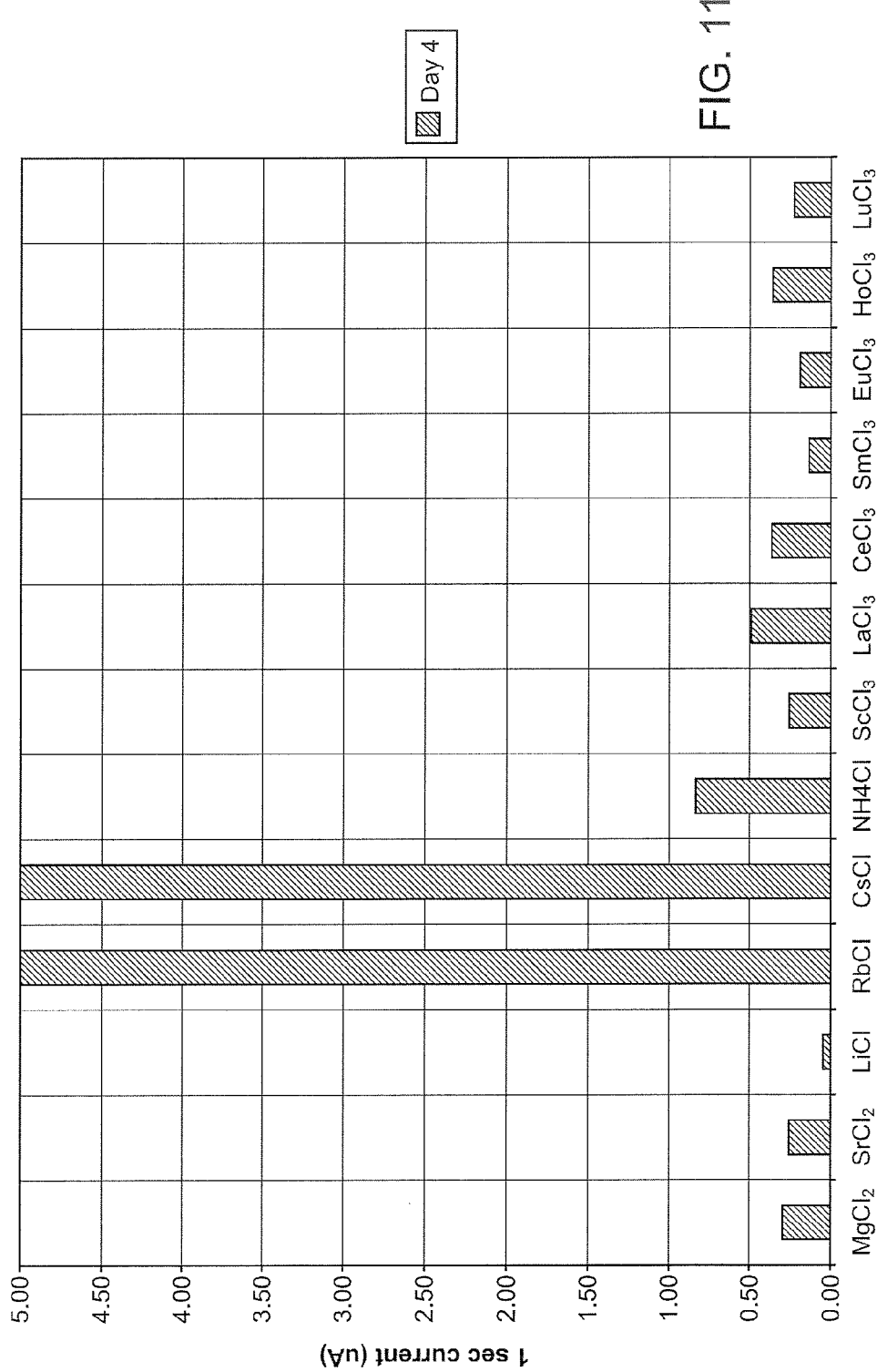
FIG. 11 illustrates that strontium ions and the lanthanide metal ions (lanthanum, cerium, samarium, europium, holmium, lutetium) have a good stabilizing effect in the NAD-GDH system comparable to lithium and magnesium while rubidium and caesium were poor. Again, lithium was the best stabilizing ion.

FIG. 11 shows that strontium ions and the lanthanide metal ions (lanthanum, cerium, samarium, europium, holmium, lutetium) have a good stabilizing effect in the NAD-GDH system comparable to lithium and magnesium while rubidium and caesium were poor. Again, lithium was the best stabilizing ion.

Figure 12:
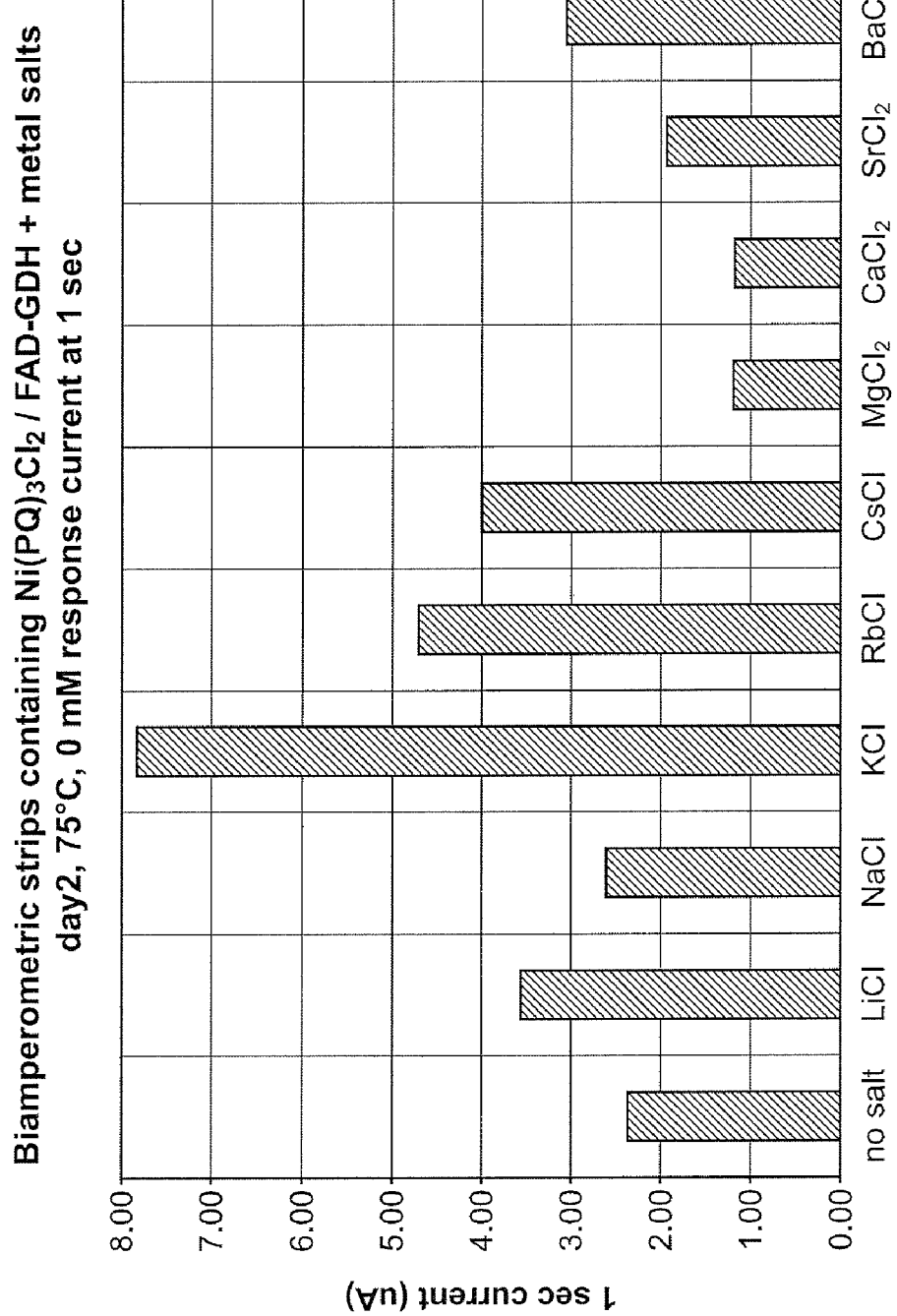
FIG. 12 illustrates that magnesium and calcium ions are the most effective stabilizing ions in the FAD-GDH system compared to the Group I alkali metal ions lithium, sodium, potassium, rubidium and caesium.

FIG. 12 shows that magnesium and calcium ions are the most effective stabilizing ions in the FAD-GDH system compared to the Group I alkali metal ions lithium, sodium, potassium, rubidium and caesium.

Figure 13:
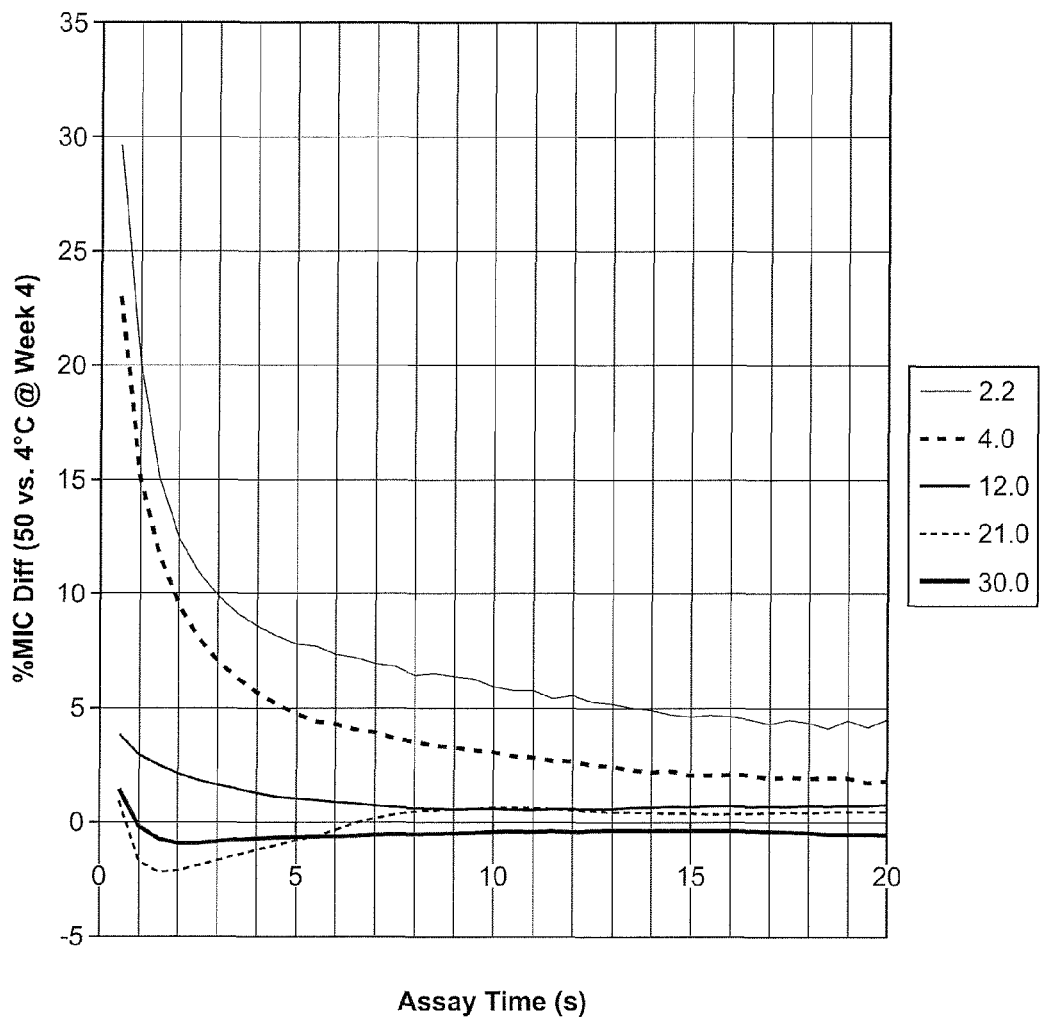
FIG. 13 illustrates the resulting % biases (% mean integrated current differences) at 4 weeks between the 50° C. and 4° C. electrodes as a function of assay time. A bias of $\leq 10\%$ is maintained at all glucose levels for assay times of $\geq 3$ seconds indicating that the $Ni(PQ)_3Cl_2$/NAD-GDH electrodes containing lithium chloride as a stabilizer have acceptable response stability in this accelerated ageing test.

E. Assessment of the 50° C. Stability of Electrodes Containing $Ni(PQ)_3Cl_2$/NAD-GDH and Formulated with Lithium Chloride as Stabilizer Gold electrodes were slot-coated with a reagent formulation containing 0.7% lithium chloride. The electrodes were then stored at 4° C. and 50° C. for 4 weeks before being tested for response to glucose in control solution. FIG. 13 below displays the resulting % biases (% mean integrated current differences) at 4 weeks between the 50° C. and 4° C. electrodes as a function of assay time. A bias of $\leq 10\%$ is maintained at all glucose levels for assay times of $\geq 3$ seconds indicating that the electrodes containing lithium chloride as a stabilizer have acceptable response stability in this accelerated ageing test.

Aspects and embodiments of the invention will be more fully understood by reference to the following examples. They should not, however, be construed as limiting the scope of the invention. All literature citations are incorporated herein by reference in their entirety.

The preceding merely illustrates principles of various aspects of the invention. It will be appreciated that those skilled in the art will be able to devise various arrangements which, although not explicitly described or shown herein, embody the principles of embodiments of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the claimed subject matter as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the presently claimed subject matter, therefore, is not intended to be limited to the exemplary embodiments shown and described herein. Rather, the scope and spirit of the presently claimed subject matter is embodied by the appended claims.

That which is claimed is:

1. A composition for use in stabilizing a biosensor, comprising:
    a. an enzyme and a co-factor, and
    b. a redox mediator complex comprising:
        i. a first metal ion covalently bonded to at least one compound comprising a 1,2-quinone moiety; and
        ii. a second metal ion non-covalently bonded to oxygen atoms of the 1,2-quinone moiety.

2. The composition of claim 1, wherein the first metal ion is selected from the group consisting of nickel, manganese, iron, cobalt, osmium, or ruthenium.

3. The composition of claim 1, wherein the ratio of the second metal ion to redox mediator complex is at least 1:1.

4. The composition of claim 1, wherein the at least one compound comprising a 1,2-quinone moiety is 1,10-phenanthroline quinone, or a derivative thereof.

5. The method of claim 1, wherein the enzyme is selected from the group consisting of an NAD(P)+-dependent dehydrogenase, a PQQ-glucose dehydrogenase, an FAD-glucose dehydrogenase and a glucose oxidase.

6. The method of claim 5, wherein the NAD(P)+-dependent dehydrogenase is glucose hydrogenase or hydroxybutyrate dehydrogenase.

7. The composition of claim 1 wherein the redox mediator complex comprises $[Ni(PQ)_3]^{2+}$.

8. A method for stabilizing a redox mediator complex, comprising:
    adding a first metal ion to a redox mediator complex, wherein the redox mediator complex comprises a second metal ion covalently bonded to at least one compound comprising a 1,2-quinone moiety and wherein the added first metal ion non-covalently bonds to oxygen atoms of the 1,2-quinone moiety.

9. The method of claim 8, wherein the first metal ion is selected from the group consisting of lithium, scandium, yttrium, lanthanum, cerium, praseodymium, neodymium, promethium, samarium, europium, gadolinium, terbium, dysprosium, holmium, erbium, thulium, ytterbium and lutetium.

10. The method of claim 8, wherein the second metal ion is selected from the group consisting of nickel, manganese, iron, cobalt, osmium, or ruthenium.

11. The method of claim 8, wherein the ratio of first metal ion to redox mediator complex is at least 1:1.

12. The method of claim 8 wherein the redox mediator complex comprises $[Ni(PQ)_3]^{2+}$.

13. A biosensor strip comprising:
   a. an electrode support;
   b. a first electrode disposed on the electrode support, the first electrode being a working electrode,
   c. a second electrode disposed on the electrode support, the second electrode being a reference electrode; and
   d. a reagent composition deposited over the first electrode and second electrode, wherein the reagent composition comprises:
      i. an enzyme, and
      ii. a redox mediator complex comprising:
         a) a first metal ion covalently bonded to at least one compound comprising a 1,2-quinone moiety; and
         b) a second metal ion non-covalently bonded to oxygen atoms of the 1,2-quinone moiety.

14. The biosensor strip of claim 13, wherein the second metal ion is selected from the group consisting of lithium, scandium, yttrium, lanthanum, cerium, praseodymium, neodymium, promethium, samarium, europium, gadolinium, terbium, dysprosium, holmium, erbium, thulium, ytterbium and lutetium, but not sodium, potassium, rubidium, cesium, all other transition metals or a quaternary ammonium counter ion.

15. The biosensor strip of claim 13 wherein the redox mediator complex comprises $[Ni(PQ)_3]^{2+}$.

16. An analyte test kit comprising:
   a. a meter for measuring the concentration of an analyte, and
   b. a biosensor strip, further comprising:
      i. an electrode support;
      ii. a first electrode disposed on the electrode support, the first electrode being a working electrode;
      iii. a second electrode disposed on the electrode support, the second electrode being a reference electrode; and
      iv. a reagent composition deposited over the first electrode and second electrode, wherein the reagent composition comprises:
         a) an enzyme, and
         b) a redox mediator complex comprising:
            i) a first metal ion covalently bonded to at least one compound comprising a 1,2-quinone moiety; and
            ii) a second metal ion non-covalently bonded to oxygen atoms of the 1,2-quinone moiety.

17. The analyte test kit of claim 16 wherein the redox mediator complex comprises $[Ni(PQ)_3]^{2+}$.

* * * * *